US010752898B2

(12) United States Patent
Pietri-Rouxel et al.

(10) Patent No.: US 10,752,898 B2
(45) Date of Patent: Aug. 25, 2020

(54) EFFECTIVE GENE THERAPY TOOLS FOR DYSTROPHIN EXON 53 SKIPPING

(71) Applicant: GENETHON, Evry (FR)

(72) Inventors: France Pietri-Rouxel, Clichy la Garenne (FR); Virginie Francois, Remouille (FR)

(73) Assignee: GENETHON, Evry (FR)

( * ) Notice: Subject to any disclaimer, the term of this patent is extended or adjusted under 35 U.S.C. 154(b) by 102 days.

(21) Appl. No.: 16/060,396

(22) PCT Filed: Dec. 9, 2016

(86) PCT No.: PCT/FR2016/053312
§ 371 (c)(1),
(2) Date: Jun. 7, 2018

(87) PCT Pub. No.: WO2017/098187
PCT Pub. Date: Jun. 15, 2017

(65) Prior Publication Data
US 2018/0362980 A1 Dec. 20, 2018

(30) Foreign Application Priority Data
Dec. 9, 2015 (FR) ...................... 15 62036

(51) Int. Cl.
C12N 15/113 (2010.01)
A61P 21/00 (2006.01)
A61K 48/00 (2006.01)
C12N 15/62 (2006.01)

(52) U.S. Cl.
CPC ........ *C12N 15/113* (2013.01); *A61K 48/0058* (2013.01); *A61K 48/0066* (2013.01); *A61P 21/00* (2018.01); *C12N 15/62* (2013.01); *C12N 2310/11* (2013.01); *C12N 2320/33* (2013.01)

(58) Field of Classification Search
CPC ... C12N 15/111; C12N 15/113; C12N 15/907; C12N 2320/33; C12N 2310/11; C12N 2800/80
USPC ...... 514/44; 435/6.1, 6.11, 91.1, 91.31, 455, 435/458; 536/23.1, 24.5
See application file for complete search history.

(56) References Cited

U.S. PATENT DOCUMENTS

| 6,156,303 | A | 12/2000 | Russell et al. |
| 7,282,199 | B2 | 10/2007 | Gao et al. |
| 2003/0228282 | A1 | 12/2003 | Gao et al. |
| 2010/0168212 | A1 | 7/2010 | Popplewell et al. |
| 2014/0315977 | A1 | 10/2014 | Bestwick et al. |
| 2019/0017048 | A1 * | 1/2019 | Van Wyk ............. C12N 15/113 |

FOREIGN PATENT DOCUMENTS

| WO | WO 03042397 A2 | 5/2003 | | |
| WO | WO 2004/083446 A2 | 9/2004 | | |
| WO | WO 2005/033321 A2 | 4/2005 | | |
| WO | WO 2006/000057 A1 | 1/2006 | | |
| WO | WO 2006/021724 A2 | 3/2006 | | |
| WO | WO 2011/057350 A1 | 5/2011 | | |
| WO | WO-2011057350 A1 * | 5/2011 | ........... | C12N 15/111 |
| WO | WO 2011/113889 A1 | 9/2011 | | |
| WO | WO 2012/029986 A1 | 10/2013 | | |
| WO | WO-2014007620 A2 * | 1/2014 | ........... | C12N 15/113 |
| WO | WO 2014/100714 A1 | 6/2014 | | |

OTHER PUBLICATIONS

Arruda et al., "Peripheral Transvenular Delivery of Adeno-Associated Viral Vectors to Skeletal Muscle as a Novel Therapy for Hemophilia B.," Blood, Jun. 10, 2010, pp. 4678-4688, vol. 115, No. 23.
Ayuso et al., "Manufacturing and Characterization of a Recombinant Adeno-Associated Virus Type 8 Reference Standard Material," Human Gene Therapy, Nov. 2014, pp. 977-987, vol. 25, No. 11.
Chaouch et al., "Immortalized Skin Fibroblasts Expressing Conditional MyoD as a Renewable and Reliable Source of Converted Human Muscle Cells to Assess Therapeutic Strategies for Muscular Dystrophies: Validation of an Exon-Skipping Approach to Restore Dystrophin in Duchenne Muscular Dystrophy Cells," Human Gene Therapy, Jul. 2009, pp. 784-790, vol. 20, No. 7.
Cooper et al., "Dystrophinopathy Carrier Determination and Detection of Protein Deficiencies in Muscular Dystrophy Using Lentiviral MyoD-Forced Myogenesis," Neuromuscular Disorders, Apr. 2007, pp. 276-284, vol. 17, No. 4.
Echigoya et al., "In Silico Screening Based on Predictive Algorithms as a Design Tool for Exon Skipping Oligonucleotides in Duchenne Muscular Dystrophy," PLos One, Mar. 27, 2015, vol. 10, No. 3.
Grimm et al., "The Low Abundance of U7 snRNA is Partly Determined by its Sm Binding Site," The EMBO Journal, Mar. 1993, pp. 1229-1238, vol. 12, No. 3.
Goyenvalle et al., "Enhanced Exon-Skipping Induced by U7 snRNA Carrying a Splicing Silencer Sequence: Promising Tool for DMD Therapy," Molecular Therapy, Jul. 2009, pp. 1234-1240, vol. 17, No. 7.
Hernandez, "Small Nuclear RNA Genes: A Model System to Study Fundamental mechanisms of Transcription," Journal of Biological Chemistry, Jul. 20, 2001, pp. 26733-26736, vol. 276.
International Search Report dated Mar. 23, 2017 for PCT Application No. PCT/FR2016/053312.

(Continued)

Primary Examiner — Jane J Zara
(74) Attorney, Agent, or Firm — Knobbe, Martens, Olson & Bear LLP

(57) ABSTRACT

The invention relates to a recombinant adeno-associated viral vector (rAAV) comprising a sequence encoding an antisense oligonucleotide (AON) directed against a segment of at least 33 bases from the +30 to +69 region of exon 53 of the pre-messenger RNA (pre-mRNA) of dystrophin, advantageously of human origin, and to the use thereof as a drug, in particular for the treatment of Duchenne muscular dystrophy (DMD).

15 Claims, 6 Drawing Sheets
Specification includes a Sequence Listing.

(56) References Cited

OTHER PUBLICATIONS

Le Guiner et al., "Forelimb Treatment in a Large Cohort of Dystrophic Dogs Support Delivery of a Recombinant AAV for Exon Skipping in Duchenne Patients," Molecular Therapy, Nov. 2014, pp. 1923-1935, vol. 22, No. 11.

Moser, "Duchenne Muscular Dystrophy: Pathogenetic Aspects and Genetic Prevention," Human Genetics, 1984, pp. 17-40, vol. 66, No. 1.

Popplewell et al., "Comparative Analysis of Antisense Oligonucleotide Sequences Targeting Exon 53 of the Human DMD Gene: Implications for Future Clinical Trials," Neuromuscular Disorders, Feb. 1, 2010, pp. 102-110, vol. 20, No. 2, Pergamon Press, GB.

Popplewell et al., "Design of Phosphorodiamidate Morpholino Oligomers (PMOs) for the Induction of Exon Skipping of the Human DMD Gene," The American Society of Gene Therapy, Mar. 2009, pp. 554-561, vol. 17, No. 3.

Sambrook et al., "Molecular Cloning: A Laboratory Manual," $2^{nd}$ ed., 1989, Cold Spring Harbor Laboratory Press, New York.

Schumperli et al., "The Special Sm Core Structure of the U7 snRNP: Far-Reaching Significance of a Small Nuclear Ribonucleoprotein," Cellular and Molecular Life Sciences, Oct. 2004, pp. 2560-2570, vol. 61, Issue 19-20.

Sharma et al., "Stem-Loop 4 of U1 snRNA is Essential for Splicing and Interacts with the U2 snRNP-Specific SF3A1 Protein During Spliceosome Assembly," Genes & Development, Nov. 15, 2014, pp. 2518-2531, vol. 28, No. 22.

Toromanoff et al., "Safety and Efficacy of Regional Intravenous (r.i.) Versus Intramuscular (i.m.) Delivery of rAAV1 and rAAV8 to Nonhuman Primate Skeletal Muscle," Molecular Therapy, Jul. 2008, pp. 1291-1299, vol. 16, No. 7.

Zheng et al., "Safety and Feasibility of High-Pressure Transvenous Limb Perfusion with 0.9% Saline in Human Muscular Dystrophy," Molecular Therapy, Feb. 2012, pp. 456-461, vol. 20, No. 2.

\* cited by examiner

A/

Dys3-9

18S

B/

Dystrophine
Dysferline

A/

Dys3-9

18S

B/

Dystrophine
Dysferline

```
                    SEQUENCE LISTING

<160> NUMBER OF SEQ ID NOS: 38

<210> SEQ ID NO 1
<211> LENGTH: 212
<212> TYPE: DNA
<213> ORGANISM: Homo sapiens
<220> FEATURE:
<223> OTHER INFORMATION: Dystrophin exon 53

<400> SEQUENCE: 1
ttgaaagaat tcagaatcag tgggatgaag tacaagaaca ccttcagaac cggaggcaac      60
agttgaatga aatgttaaag gattcaacac aatggctgga agctaaggaa gaagctgagc     120
aggtcttagg acaggccaga gccaagcttg agtcatggaa ggagggtccc tatacagtag     180
atgcaatcca aaagaaaatc acagaaacca ag                                   212

<210> SEQ ID NO 2
<211> LENGTH: 442
<212> TYPE: DNA
<213> ORGANISM: Artificial Sequence
<220> FEATURE:
<223> OTHER INFORMATION: U7-JR53

<400> SEQUENCE: 2
```

```
taacaacata ggagctgtga ttggctgttt tcagccaatc agcactgact catttgcata    60
gcctttacaa gcggtcacaa actcaagaaa cgagcggttt taatagtctt ttagaatatt   120
gtttatcgaa ccgaataagg aactgtgctt tgtgattcac atatcagtgg aggggtgtgg   180
aaatggcacc ttgatctcac cctcatcgaa agtggagttg atgtccttcc ctggctcgct   240
acagacgcac ttccgcaaca ttcaactgtt gcctccggtt ctgaaggtgt tcttgtacaa   300
tttttggagc aggttttctg acttcggtcg gaaaacccct cccaatttca ctggtctaca   360
atgaaagcaa aacagttctc ttccccgctc cccggtgtgt gagagggct tgatccttc    420 tctggtttcc taggaaacgc gt                                            442

<210> SEQ ID NO 3
<211> LENGTH: 40
<212> TYPE: DNA
<213> ORGANISM: Artificial Sequence
<220> FEATURE:
<223> OTHER INFORMATION: JR53

<400> SEQUENCE: 3
cattcaactg ttgcctccgg ttctgaaggt gttcttgtac                          40

<210> SEQ ID NO 4
<211> LENGTH: 33
<212> TYPE: DNA
<213> ORGANISM: Artificial Sequence
<220> FEATURE:
<223> OTHER INFORMATION: N3

<400> SEQUENCE: 4
caactgttgc ctccggttct gaaggtgttc ttg                                 33

<210> SEQ ID NO 5
<211> LENGTH: 24
<212> TYPE: DNA
<213> ORGANISM: Artificial Sequence
<220> FEATURE:
<223> OTHER INFORMATION: N2

<400> SEQUENCE: 5
ttgcctccgg ttctgaaggt gttc                                           24

<210> SEQ ID NO 6
<211> LENGTH: 27
<212> TYPE: DNA
<213> ORGANISM: Artificial Sequence
<220> FEATURE:
<223> OTHER INFORMATION: N1

<400> SEQUENCE: 6
ttgcctccgg ttctgaaggt gttcttg                                        27

<210> SEQ ID NO 7
<211> LENGTH: 30
<212> TYPE: DNA
<213> ORGANISM: Artificial Sequence
<220> FEATURE:
<223> OTHER INFORMATION: Di/I

<400> SEQUENCE: 7
caactgttgc ctccggttct gaaggtgttc                                     30

<210> SEQ ID NO 8
```

<211> LENGTH: 36
<212> TYPE: DNA
<213> ORGANISM: Artificial Sequence
<220> FEATURE:
<223> OTHER INFORMATION: Dtex53

<400> SEQUENCE: 8

```
ttggctctgg cctgtcctct gttgcctccg gttctg                              36
```

<210> SEQ ID NO 9
<211> LENGTH: 19
<212> TYPE: DNA
<213> ORGANISM: Artificial Sequence
<220> FEATURE:
<223> OTHER INFORMATION: Scramble

<400> SEQUENCE: 9

```
ggtgtattgc atgatatgt                                                 19
```

<210> SEQ ID NO 10
<211> LENGTH: 812
<212> TYPE: DNA
<213> ORGANISM: Artificial Sequence
<220> FEATURE:
<223> OTHER INFORMATION: ITR-U7-JR53

<400> SEQUENCE: 10

```
ctgcgcgctc gctcgctcac tgaggccgcc cgggcaaagc ccgggcgtcg ggcgaccttt     60
ggtcgcccgg cctcagtgag cgagcgagcg cgcagagagg gagtggccaa ctccatcact    120
aggggttcct tgtagttaat gattaacccg ccatgctact tatctacgta gccatgctct    180
agataacaac ataggagctg tgattggctg ttttcagcca atcagcactg actcatttgc    240
atagccttta caagcggtca caaactcaag aaacgagcgg ttttaatagt cttttagaat    300
attgtttatc gaaccgaata aggaactgtg ctttgtgatt cacatatcag tggaggggtg    360
tggaaatggc accttgatct caccctcatc gaaagtggag ttgatgtcct tccctggctc    420
gctacagacg cacttccgca acattcaact gttgcctccg gttctgaagg tgttcttgta    480
caatttttgg agcaggtttt ctgacttcgg tcggaaaacc cctcccaatt tcactggtct    540
acaatgaaag caaaacagtt ctcttccccg ctccccggtg tgtgagaggg gctttgatcc    600
ttctctggtt tcctaggaaa cgcgttgtcg ctagagcatg gctacgtaga taagtagcat    660
ggcgggttaa tcattaacta caaggaaccc ctagtgatgg agttggccac tccctctctg    720
cgcgctcgct cgctcactga ggccgggcga ccaaaggtcg cccgacgccc gggctttgcc    780
cgggcggcct cagtgagcga gcgagcgcgc ca                                  812
```

<210> SEQ ID NO 11
<211> LENGTH: 18
<212> TYPE: DNA
<213> ORGANISM: Artificial Sequence
<220> FEATURE:
<223> OTHER INFORMATION: AAV18mers.R

<400> SEQUENCE: 11

```
gtagataagt agcatggc                                                  18
```

<210> SEQ ID NO 12
<211> LENGTH: 22
<212> TYPE: DNA
<213> ORGANISM: Artificial Sequence
<220> FEATURE:
<223> OTHER INFORMATION: AAV18mers.F

```
<400> SEQUENCE: 12
ctccatcact aggggttcct tg                                              22

<210> SEQ ID NO 13
<211> LENGTH: 17
<212> TYPE: DNA
<213> ORGANISM: Artificial Sequence
<220> FEATURE:
<223> OTHER INFORMATION: AAV_M G B.P

<400> SEQUENCE: 13
tagttaatga ttaaccc                                                    17

<210> SEQ ID NO 14
<211> LENGTH: 22
<212> TYPE: DNA
<213> ORGANISM: Artificial Sequence
<220> FEATURE:
<223> OTHER INFORMATION: Alb.F

<400> SEQUENCE: 14
gctgtcatct cttgtgggct gt                                              22

<210> SEQ ID NO 15
<211> LENGTH: 21
<212> TYPE: DNA
<213> ORGANISM: Artificial Sequence
<220> FEATURE:
<223> OTHER INFORMATION: Alb.R

<400> SEQUENCE: 15
actcatggga gctgctggtt c                                               21

<210> SEQ ID NO 16
<211> LENGTH: 26
<212> TYPE: DNA
<213> ORGANISM: Artificial Sequence
<220> FEATURE:
<223> OTHER INFORMATION: AlbVIC.P

<400> SEQUENCE: 16
cctgtcatgc ccacacaaat ctctcc                                          26

<210> SEQ ID NO 17
<211> LENGTH: 20
<212> TYPE: DNA
<213> ORGANISM: Artificial Sequence
<220> FEATURE:
<223> OTHER INFORMATION: ex51 hDMD Fext

<400> SEQUENCE: 17
gttactctgg tgacacaacc                                                 20

<210> SEQ ID NO 18
<211> LENGTH: 20
<212> TYPE: DNA
<213> ORGANISM: Artificial Sequence
<220> FEATURE:
<223> OTHER INFORMATION: ex54hDMD Rext

<400> SEQUENCE: 18
atgtggactt ttctggtatc                                                 20

<210> SEQ ID NO 19
```

```
<211> LENGTH: 20
<212> TYPE: DNA
<213> ORGANISM: Artificial Sequence
<220> FEATURE:
<223> OTHER INFORMATION: ex51 hDMD Fint

<400> SEQUENCE: 19
actagaaatg ccatcttcct                                              20

<210> SEQ ID NO 20
<211> LENGTH: 20
<212> TYPE: DNA
<213> ORGANISM: Artificial Sequence
<220> FEATURE:
<223> OTHER INFORMATION: ex54 hDMD Rint

<400> SEQUENCE: 20
caagtcattt gccacatcta                                              20

<210> SEQ ID NO 21
<211> LENGTH: 19
<212> TYPE: DNA
<213> ORGANISM: Artificial Sequence
<220> FEATURE:
<223> OTHER INFORMATION: Dys43-F

<400> SEQUENCE: 21
cctgtggaaa gggtgaagc                                               19

<210> SEQ ID NO 22
<211> LENGTH: 21
<212> TYPE: DNA
<213> ORGANISM: Artificial Sequence
<220> FEATURE:
<223> OTHER INFORMATION: Dys44-F

<400> SEQUENCE: 22
cgatttgaca gatctgttga g                                            21

<210> SEQ ID NO 23
<211> LENGTH: 20
<212> TYPE: DNA
<213> ORGANISM: Artificial Sequence
<220> FEATURE:
<223> OTHER INFORMATION: Dys56-R

<400> SEQUENCE: 23
tgagagactt tttccgaagt                                              20

<210> SEQ ID NO 24
<211> LENGTH: 20
<212> TYPE: DNA
<213> ORGANISM: Artificial Sequence
<220> FEATURE:
<223> OTHER INFORMATION: Dys57-R

<400> SEQUENCE: 24
aagttcctgc agagaaaggt                                              20

<210> SEQ ID NO 25
<211> LENGTH: 23
<212> TYPE: DNA
<213> ORGANISM: Artificial Sequence
<220> FEATURE:
<223> OTHER INFORMATION: hDys-44/54-F

<400> SEQUENCE: 25
```

```
cctgagaatt gggaacatgc taa                                              23

<210> SEQ ID NO 26
<211> LENGTH: 18
<212> TYPE: DNA
<213> ORGANISM: Artificial Sequence
<220> FEATURE:
<223> OTHER INFORMATION: hDys-44/54-R

<400> SEQUENCE: 26
gccactggcg gaggtctt                                                    18

<210> SEQ ID NO 27
<211> LENGTH: 19
<212> TYPE: DNA
<213> ORGANISM: Artificial Sequence
<220> FEATURE:
<223> OTHER INFORMATION: hDys-44/54-P

<400> SEQUENCE: 27
ggtatcttaa gcagttggc                                                   19

<210> SEQ ID NO 28
<211> LENGTH: 24
<212> TYPE: DNA
<213> ORGANISM: Artificial Sequence
<220> FEATURE:
<223> OTHER INFORMATION: hDys-4/5-F

<400> SEQUENCE: 28
catgccctga acaatgtcaa caag                                             24

<210> SEQ ID NO 29
<211> LENGTH: 25
<212> TYPE: DNA
<213> ORGANISM: Artificial Sequence
<220> FEATURE:
<223> OTHER INFORMATION: hDys-4/5-R

<400> SEQUENCE: 29
tccatctacg atgtcagtac ttcca                                            25

<210> SEQ ID NO 30
<211> LENGTH: 24
<212> TYPE: DNA
<213> ORGANISM: Artificial Sequence
<220> FEATURE:
<223> OTHER INFORMATION: hDys-4/5-P

<400> SEQUENCE: 30
ttgcagaaca ataatgttga ttta                                             24

<210> SEQ ID NO 31
<211> LENGTH: 20
<212> TYPE: DNA
<213> ORGANISM: Artificial Sequence
<220> FEATURE:
<223> OTHER INFORMATION: Dys49-F

<400> SEQUENCE: 31
caaccggatg tggaagagat                                                  20

<210> SEQ ID NO 32
<211> LENGTH: 20
<212> TYPE: DNA
```

```
<213> ORGANISM: Artificial Sequence
<220> FEATURE:
<223> OTHER INFORMATION: Dys50-F

<400> SEQUENCE: 32
ctctgagtgg aaggcggtaa                                                    20

<210> SEQ ID NO 33
<211> LENGTH: 20
<212> TYPE: DNA
<213> ORGANISM: Artificial Sequence
<220> FEATURE:
<223> OTHER INFORMATION: PO -F

<400> SEQUENCE: 33
ggcgagctgg aagtgcaact                                                    20

<210> SEQ ID NO 34
<211> LENGTH: 20
<212> TYPE: DNA
<213> ORGANISM: Artificial Sequence
<220> FEATURE:
<223> OTHER INFORMATION: PO-R

<400> SEQUENCE: 34
ccatcagcac cacagccttc                                                    20

<210> SEQ ID NO 35
<211> LENGTH: 24
<212> TYPE: DNA
<213> ORGANISM: Artificial Sequence
<220> FEATURE:
<223> OTHER INFORMATION: 18S-F

<400> SEQUENCE: 35
tcaagaacga aagtcggagg ttcg                                               24

<210> SEQ ID NO 36
<211> LENGTH: 23
<212> TYPE: DNA
<213> ORGANISM: Artificial Sequence
<220> FEATURE:
<223> OTHER INFORMATION: 18S-R

<400> SEQUENCE: 36
ttatgctcaa tctcgggtgg ctg                                                23

<210> SEQ ID NO 37
<211> LENGTH: 22
<212> TYPE: DNA
<213> ORGANISM: Artificial Sequence
<220> FEATURE:
<223> OTHER INFORMATION: Dys3-F

<400> SEQUENCE: 37
gagaacctct tcagtgacct ac                                                 22
```

```
<210> SEQ ID NO 38
<211> LENGTH: 20
<212> TYPE: DNA
<213> ORGANISM: Artificial Sequence
<220> FEATURE:
<223> OTHER INFORMATION: Dys9-R

<400> SEQUENCE: 38
gaggtggtga cataagcagc                                              20
```

EFFECTIVE GENE THERAPY TOOLS FOR DYSTROPHIN EXON 53 SKIPPING

CROSS-REFERENCE TO RELATED APPLICATIONS

This application is the U.S. National Phase under 35 U.S.C. § 371 of International Application PCT/FR2016/053312, filed Dec. 9, 2016, which claims the benefit of French Application No. 1562036, filed Dec. 9, 2015, the disclosures of which are incorporated by reference herein in their entireties.

REFERENCE TO SEQUENCE LISTING

A sequence listing submitted as an ASCII text file via EFS-Web is hereby incorporated by reference in accordance with 35 U.S.C. § 1.52(e). The name of the ASCII text file for the Sequence Listing is SeqList-LAUR006_001APC.txt, the date of creation of the ASCII text file is May 3, 2018, and the size of the ASCII text file is 9.32 KB.

BACKGROUND

The present invention relates to gene therapy tools that perform particularly well in the treatment of muscular dystrophy diseases, such as Duchenne muscular dystrophy (DMD).

This is based on the careful choice of antisense oligonucleotides (AON) making it possible to skip exon 53 of the dystrophin gene, conveyed by a recombinant adeno-associated viral vector (AAVr), and advantageously associated with a modified snRNA.

DESCRIPTION OF THE RELATED ART

Duchenne muscular dystrophy (DMD) is the most frequent degenerative progressive muscular disease. This is a genetic disease carried by the X chromosome that affects approximately 1 in 5000 boys. It results from mutations or deletions in the dystrophin gene. The non-expression or expression of a highly abnormal dystrophin generates fragility of the muscular fiber, resulting in accelerated destruction of the muscle tissue. The functional dystrophin deficit causes degeneration of the fibers, inflammation, necrosis and replacement of the muscle by adipose tissue, which causes progressive muscle weakness and premature death due to respiratory or heart failure during the second to fourth decades of life (Moser, H., Hum Genet, 1984. 66(1): 17-40).

The dmd gene (2.7 Mb), coding for the dystrophin protein, is made up of 79 exons and is located at locus 21.2 of the X chromosome. Dystrophin is a modular protein having a central region made up of 24 "spectrin-like" repeated domains.

The majority of the serious mutations of the dystrophin gene consist of deletions of one or more exons disrupting the reading frame of the final messenger, duplications of a portion of the gene, or point mutations, present in the coding regions (or exons), which introduce stop codons or shifts in the reading phase.

Yet it has been noted that truncated forms of dystrophin, in particular without certain repeated sequences, are fully functional, or at least only partially defective, like for example in the attenuated form of the disease called Becker muscular dystrophy (BMD).

Starting from this observation and as an alternative to traditional gene therapy consisting of providing an intact copy of the defective gene (which is problematic in light of the size of that coding dystrophin), different strategies have been considered to try to "repair" dysfunctional dystrophins.

Thus, exon skipping is a therapeutic approach that consists of administering antisense oligonucleotides (AON) complementary to the sequences involved in the splicing of the exons to be masked, in order to restore the reading frame. In particular, exon skipping occurring in regions of repeated sequences makes it possible to obtain a shorter dystrophin protein than the native protein, but which is nevertheless functional.

In practice, skipping exon 53 may prove beneficial in all cases where it makes it possible to restore the reading frame. This theoretically targets a large number of mutations that may be present in the dystrophin gene, in particular deletions of exon 52 (Δ52), exons 50 to 52 (Δ50-52), exons 49 to 52 (Δ49-52), exons 48 to 52 (Δ48-52), exons 47 to 52 (Δ47-52), exons 45 to 52 (Δ45-52), exons 43 to 52 (Δ43-52), exons 42 to 52 (Δ42-52), exons 41 to 52 (Δ41-52), exons 40 to 52 (Δ40-52), exons 39 to 52 (Δ39-52), exons 38 to 52 (Δ38-52), exons 37 to 52 (Δ37-52), exons 36 to 52 (Δ36-52), exons 35 to 52 (Δ35-52), exons 34 to 52 (Δ34-52), exons 33 to 52 (Δ33-52), exons 32 to 52 (Δ32-52), exons 31 to 52 (Δ31-52), exons 30 to 52 (Δ30-52), exons 29 to 52 (Δ29-52), exons 28 to 52 (Δ28-52), exons 27 to 52 (Δ27-52), exons 26 to 52 (Δ26-52), exons 25 to 52 (Δ25-52), exons 24 to 52 (Δ24-52), exons 23 to 52 (Δ23-52), exons 21 to 52 (Δ21-52) and exons 10 to 52 (Δ10-52), or the duplication of exon 53.

Thus, this strategy in particular makes it possible to consider treating different identified forms of DMD, in particular those associated with deletions of exon 52 (Δ52), exons 50 to 52 (Δ50-52), exons 49 to 52 (Δ49-52), exons 48 to 52 (Δ48-52), exons 47 to 52 (Δ47-52), exons 46 to 52 (Δ46-52), exons 45 to 52 (Δ45-52), exons 43 to 52 (Δ43-52) and exons 10 to 52 (Δ10-52), or with a duplication of exon 53.

One of the challenges of this technology consists of stably and lastingly introducing an antisense oligonucleotide into sick muscle fibers.

It has been considered to inject said AONs directly, in naked form. However, in light of the short lifetime these oligonucleotides have in muscle, this treatment mode requires regular, relatively restrictive injections. Developments have chemically modified these oligonucleotides (morpholinos, 2'O methyl, inosine derivatives, etc.). This approach effectively makes it possible to stabilize them in vivo, and thus to improve their efficacy and space apart their injection. However and at high doses, this type of oligonucleotide may prove toxic.

Alternatively, attempts have been made to express in situ these sequences via expression vectors making it possible to convey them in the target cells. Adeno-associated recombinant viral vectors (or AAVr) have proven particularly suitable for transduction in muscles. These vectors allow the in vivo transfer of an expression cassette bearing the sequence coding the AON and leading to the continuous synthesis of this AON in vivo. Thus, the injection of these vectors has the advantage of allowing a restoration of the expression of the protein over the long term. As an example, Le Guiner et al. (Molecular Therapy, 2014, 22(11)1923-35) reported significant efficacy of exon skipping coupled with the use of a recombinant AAV8, even 3.5 months after loco-regional administration in dystrophic dogs.

In this context, the use of sequences derived from snRNA ("small nucleotide RNA") in these vectors, in which the antisense sequences are inserted, has made it possible to limit the deterioration of the AONs in vivo, increasing the efficacy of treatments over time even more. This strategy was in particular described in application WO 2006/021724, reporting the use of U7-type snRNA (U7snRNA) to transport AONs targeting the dystrophin gene.

The characteristics of snRNAs make them high-performing tools for the stable and nuclear expression of AON sequences. Indeed, the corresponding genes are small, expressed stably and continuously at the nuclear level and target the early stages of the transcription (pre-mRNA). In practice and relative to U7snRNA, this involves inserting AON sequences in the binding sites of the Sm proteins in the snRNA, such that they no longer target the pre-messenger RNAs of the histones, but the exon(s) of the targeted gene of interest, thereby blocking the splicing consensus sites and making it possible to correct or modify the maturation of this gene.

It has moreover been suggested to add to these snRNA sequences, sequences called "exon splicing enhancer" sequences, allowing the bonding of factors involved in the splicing (in particular the hnRNPA1 protein, for "heterogeneous ribonucleoprotein A1"), in order to further improve the observed therapeutic effects (Goyenvalle et al., Mol Ther.; 17(7): 1234-1240, 2009).

The fact remains that the choice of AONs, and therefore sequences coding these AONs in the case of vectors, is critical and has proven particularly complex. Indeed, it is difficult to predict which sequence will be effective. Depending on the targeted exons, the effective sequences appear to vary and not relate to the same sites. This phenomenon makes the choice of the AON sequences particularly delicate and cumbersome, even using complex algorithms (Echigoya et al., Plos One, Mar. 27, 2015, DOI: 10.1371/journal.pone.0120058).

Thus and relative to exon 53, many antisenses have been proposed, varying in terms of both the region of the targeted exon and the size of the oligonucleotide in question. Candidate antisense sequences have for example been proposed in the following documents: WO2004/083446, WO2006/000057, US2010/0168212, WO2011/057350, WO2012/029986, WO2014/100714, US 2014/315977, Popelwell et al. (Mol Ther. 2009 March; 17(3):554-61; Neuromuscul Disord. 2010 February; 20(2):102-10). Variable efficacy of these sequences, tested in the form of naked or optionally modified oligonucleotides, possibly in combination, has been described in these documents.

In light of the clinical challenges, the need still exists to develop an optimized tool targeting exon 53 skipping on the messenger RNA coding dystrophin, i.e., allowing effective skipping of said exon and a high expression level of the corresponding protein, truncated but potentially functional.

SUMMARY

The present invention aims to treat or improve the forms of Duchenne Muscular Dystrophy (DMD), in which skipping exon 53 on the messenger RNA coding dystrophin makes it possible to obtain a protein that is truncated, but at least partially functional.

The proposed solution is based on antisense oligonucleotides (AON), carefully chosen in terms of both the region of the exon that they target and their size. The corresponding sequences are introduced into a high-performing expression system, made up of an adeno-associated recombinant viral vector (AAVr) advantageously comprising a snRNA, preferably of type U7, advantageously modified at the binding site of the Sm proteins.

Such vectorized antisense oligonucleotides have made it possible to obtain an efficacy, in terms of both the expression of transcripts without exon 53 and the production of truncated dystrophin, never yet achieved to the knowledge of the Applicant, and therefore constitute a very promising clinical tool.

Definitions

The definitions below correspond to the meaning generally used in the context of the invention and should be taken into account, unless another definition is explicitly indicated.

Within the meaning of the invention, the articles "a" and "an" are used to refer to one or more (for example, at least one) units of the grammatical subject of the article. As an example, "an element" refers to at least one element, i.e., one or more elements.

The terms "about" or "approximately", used in reference to a measurable value such as a quantity, a duration, and other similar values, must be understood as encompassing measuring uncertainties of ±20% or ±10%, preferably ±5%, still more preferably ±1%, and particularly preferably ±0.1% of the specified value.

Intervals: throughout the present description, the various features of the invention may be presented in the form of intervals of values. It must be understood that the description of values in the form of intervals is intended solely to make reading easier and must not be interpreted as a rigid limitation of the scope of the invention. As a result, the description of an interval of values should be considered as specifically disclosing all of the possible intermediate intervals as well as each of the values within this interval. For example, the description of an interval from 1 to 6 should be considered as specifically describing each of the intervals that it comprises, such as the intervals from 1 to 3, from 1 to 4, from 1 to 5, from 2 to 4, from 2 to 6, from 3 to 6, etc., as well as each of the values in this interval, for example 1, 2, 2.7, 3, 4, 5, 5.3 and 6. This definition is valid independently of the scope of the interval.

The term "isolated" must be understood in the context of the invention as being synonymous with withdrawn or removed from its natural environment or state. For example, an isolated nucleic acid or peptide is a nucleic acid or peptide taken out of the natural environment in which it is typically found, whether it involves a plant or a living animal, for example. Thus, a nucleic acid or a peptide naturally present in a living animal is not an isolated nucleic acid or peptide within the meaning of the present invention, while the same nucleic acid or peptide, partially or completely separated from the other elements present in its natural context, is in turn "isolated" within the meaning of the invention. An isolated nucleic acid or peptide may exist in a substantially purified form, or may exist in a non-native environment, for example a host cell.

In the context of the invention, the following abbreviations are used for the most common nucleic acid bases. "A" refers to adenosine, "C" refers to cytosine, "G" refers to guanosine, "T" refers to thymidine, and "U" refers to uridine.

Unless otherwise indicated, within the meaning of the invention, a "sequence of nucleotides coding for a sequence of amino acids" refers to all of the nucleotide sequences that code for the amino acid sequence, including the degenerated nucleotide sequences making it possible to obtain said sequence of amino acids. The nucleotide sequence that codes for a protein or an RNA or a cDNA may optionally comprise introns.

The terms "coding" or "coding for", "code" or "code for" refer to the property inherent to the specific sequences of nucleotides in a polynucleotide, such as a gene, a cDNA or a mRNA, to serve as a matrix for the synthesis of other polymers and macromolecules in biological processes, having either a defined sequence of nucleotides (for example rRNA, tRNA and mRNA), or a defined sequence of amino acids, and the biological properties resulting therefrom. Thus, a gene codes for a protein if the transcription and the translation of the mRNA corresponding to this gene produce the protein in a cell or another biological system. Both the coding strand, the nucleotide sequence of which is identical to the mRNA sequence and which is generally described in the sequence listings and databases, and the non-coding strand, used as matrix for the transcription of a gene or the cDNA, can be designated as coding for the protein or another product of this gene or cDNA.

The term "polynucleotide" as used in the context of the invention is defined as a chain of nucleotides. Furthermore, the nucleic acids are nucleotide polymers. Thus, the terms nucleic acids and polynucleotides as used in the context of the invention are interchangeable. It is well known in the field of molecular biology and genetic engineering that the nucleic acids are polynucleotides, which can be hydrolyzed into monomers. Nucleotides in monomer form can be hydrolyzed into nucleosides. As used in the context of the invention, the term polynucleotide refers, without limitation, to any type of nucleic acid molecules, i.e., where the nucleic acid molecules can be obtained by any means available in the art, including by recombinant means, namely the cloning of sequences of nucleic acids from a recombinant library or the genome of a cell, by using ordinary cloning technologies such as PCR, or by synthesis.

In the context of the invention, the term "oligonucleotide" refers to a polynucleotide, the size of which preferably does not exceed 100 nucleotides (or bases), or even 95, 80, 75, 70, 65, 60, 55 or even 50 nucleotides (or bases).

Within the meaning of the invention, the terms "peptide", "polypeptide" and "protein" are used interchangeably and refer to a compound made up of amino acid residues covalently bonded by peptide bonds. By definition, a protein contains at least two amino acids, without limitation regarding the maximum number of amino acids. Polypeptides indifferently comprise several peptides and/or proteins, which in turn comprise two or more amino acids linked to one another by peptide bonds. As used here, the term refers both to short chains, which are also commonly referred to in the art as peptides, oligopeptides and oligomers, for example, and longer chains, which are generally referred to in the art as proteins, many types of which exist. "Polypeptides" for example comprise biologically active fragments, substantially homologous polypeptides, oligopeptides, homodimers, heterodimers, polypeptide variants, modified polypeptides, derivatives, analogs, fusion proteins, among others. Polypeptides comprise natural peptides, recombinant peptides, synthetic peptides, or a combination thereof.

The terms "identical" or "homologous" refer to the similarity of sequence or identity of sequence between two polypeptides or between two nucleic acid molecules. When a position in each of the two compared sequences is occupied by the same amino acid monomer base or sub-unit (for example, when a position in each of the two DNA molecules is occupied by an adenine), then the molecules are homologous or identical for this position. The percentage of identity between two sequences depends on the number of corresponding positions shared by the two sequences, and corresponds to this number divided by the number of positions compared and multiplied by 100. For example, if 6 out of 10 of the positions in two paired sequences are identical, then the two sequences are 60% identical. As a general rule, the comparison is done by aligning the two sequences so as to provide maximal homology/identity.

A "vector" within the meaning of the invention is a molecular construct that comprises an isolated nucleic acid and that can be used to deliver the isolated nucleic acid to the inside of a cell. Many vectors are known in the art, including, but not limited to, linear polynucleotides, polynucleotides associated with ionic or amphiphilic compounds, plasmids and viruses. Thus, the term "vector" for example refers to a plasmid with autonomous replication or a virus. The term must also be interpreted as comprising non-plasmid or non-viral compounds that facilitate the transfer of nucleic acids into the cells, for example compounds of polylysine, liposomes, and the like. Examples of viral vectors in particular include adenoviral vectors, adeno-associated viral vectors, and retroviral vectors.

The term "expression vector" refers to a vector comprising a recombinant polynucleotide, which comprises expression control sequences operationally linked to a nucleotide sequence to be expressed. An expression vector in particular comprises expression elements acting in cis; where other elements for the expression can be provided by the host cell or by an in vitro expression system. The expression vectors within the meaning of the invention include all those known in the art, such as cosmids, plasmids (for example naked or contained in liposomes) and viruses (for example lentiviruses, retroviruses, adenoviruses and adeno-associated viruses), which incorporate the recombinant polynucleotide.

The term "promoter" as used here is defined as a DNA sequence recognized by the synthesis machinery of the cell, or the introduced synthesis machinery, necessary to initiate the specific transcription of a sequence of polynucleotides.

Within the meaning of the invention, the terms "promoter/regulator sequence" refer to a nucleic acid sequence, necessary for the expression of the polynucleotide linked operationally to the promoter/regulator sequence. In some cases, this sequence may be the base sequence of the promoter, while in other cases, this sequence may also comprise an activator sequence and other regulator elements, useful for the expression of the polynucleotide. The promoter/regulator sequence may for example be a sequence allowing the expression of the polynucleotide that is specific to a tissue, i.e., preferably being produced in that tissue.

Within the meaning of the invention, a "constitutive" promoter is a nucleotide sequence which, when operationally linked to a polynucleotide, leads to an expression of the polynucleotide under most or all of the physiological conditions of the cell.

Within the meaning of the invention, an "inducible" promoter is a nucleotide sequence which, when operationally linked to a polynucleotide, leads to an expression of the polynucleotide only when an inducer of the promoter is present in the cell.

A promoter "specific to a tissue" is a nucleotide sequence which, when operationally linked to a polynucleotide, leads to an expression of the polynucleotide in a cell preferably if the cell is a cell of the type of tissue corresponding to the promoter.

Within the meaning of the invention, the term "abnormal", when used in reference to organisms, tissues, cells or components thereof, refers to these organisms, tissues, cells or components thereof that differ by at least one observable or detectable characteristic (for example age, treatment, time of day, etc.) from the expected characteristic in corresponding so-called "normal" organisms, tissues, cells or components.

The terms "patient", "subject", "individual" and synonyms are used in the context of the invention interchangeably and refer to an animal, preferably a mammal. In certain non-limiting embodiments, the animal is a human. It may also be a mouse, rat, pig, dog or nonhuman primate (NHP), such as the macaque.

Within the meaning of the invention, a "disease" or "pathology" is a health condition of an animal in which the homeostasis of the latter is altered, and which, if the disease is not treated, continues to deteriorate. Conversely, within the meaning of the invention, a "disorder" is a health condition in which the animal is capable of maintaining its homeostasis, but in which the health condition of the animal is less favorable than what it would be without the disorder. Without treatment, a disorder does not necessarily cause a deterioration of the health condition of the animal over time.

In the context of the invention, a disease or disorder is "alleviated" or "improved" if the gravity of a symptom of the disease or disorder, or the frequency at which the symptom is felt by the subject, or both, is reduced. This also includes the disappearance of the progression of the disease, i.e., the cessation of the deterioration of the health condition. A disease or disorder is "cured" if the gravity of a symptom of the disease or disorder, or the frequency at which such a symptom is felt by the patient, or both, is eliminated.

In the context of the invention, a "therapeutic" treatment is a treatment administered to a subject who has the symptoms of a pathology, with the aim of decreasing or eliminating these symptoms.

In the context of the invention, the "treatment of a disease or disorder" refers to the reduction in the frequency or severity of at least one symptom of a disease or disorder in a subject.

Within the meaning of the invention, an "effective quantity" of a compound is the quantity of the compound that is sufficient to obtain a beneficial effect for the subject to whom the compound is administered. The expression "therapeutically effective quantity" refers to a quantity that is sufficient or effective to prevent or treat (in other words, to delay or prevent the appearance, prevent the evolution, inhibit, reduce or reverse) a disease or disorder, including to ease the symptoms of this disease or disorder.

DETAILED DESCRIPTION

According to a first aspect, the present invention relates to an adeno-associated recombinant viral vector (AAVr) comprising a sequence coding an antisense oligonucleotide (AON) directed against a segment of at least 33 bases of the +30 to +69 region of exon 53 of the pre-messenger RNA (pre-mRNA) of dystrophin.

In the context of the present application and as outlined below, the terms "directed against", "targets", "hybridizes with" and "complementary to" are used equivalently.

The AAVr vector according to the invention typically comprises 2 components:
 The packaged recombinant nucleic acid sequence, also called "genome of the AAVr." This recombinant nucleic acid sequence comprises the sequence coding the AON, this AON producing the therapeutic effect, in the case at hand the skipping of exon 53 of the pre-mRNA of dystrophin, when it is expressed in the target cell/tissue;
 the viral capsid that allows the gene transfer and a certain tissue tropism.

According to the invention, the genome of the AAVr vector therefore comprises a sequence coding an antisense oligonucleotide, or AON. This sequence advantageously assumes the form of DNA, and allows the expression of an AON capable of hybridizing with the target pre-mRNA, in the case at hand at exon 53 of the pre-mRNA of dystrophin.

Characteristically according to the invention, the antisense oligonucleotide makes it possible to skip exon 53 on the messenger RNA of the dystrophin. It must be understood that the skipping of exon 53 using the AON according to the invention is done in the splicing stage of the pre-messenger RNA of the dystrophin. In a manner known in this technical field, the chosen AON targets and hybridizes with regions involved in the splicing. In the presence of such an AON, the splicing sites "masked" by the AON are not recognized by the cellular machinery, such that the targeted exon is not integrated into the resulting messenger RNA and is therefore "skipped."

In the context of the invention, "dystrophin pre-messenger RNA" or "dystrophin pre-mRNA" refers to the transcription product of the gene coding the dystrophin protein, as obtained before the splicing step.

The present invention targets any gene encoding a dystrophin, or any organism comprising such a gene, for which the skipping of exon 53 may be of interest, namely the production of a protein that is shorter, but at least partially functional. According to one preferred embodiment, the targeted gene is the human gene for dystrophin. The human gene for dystrophin is well-documented: it has a size of 2.7 Mb and contains 79 exons. Its complete sequence is available in databases, for example in the NCBI database under reference Gene ID: 1756 or in the Ensembl database under reference ENSG00000198947.

Advantageously and in the context of the invention, "dystrophin pre-messenger RNA" refers to the pre-mRNA of dystrophin of human origin, in other words the pre-mRNA of human dystrophin.

The sequences of the pre-mRNA of human dystrophin are well known and are in particular accessible using the references indicated above in relation to the entire gene.

More specifically, the present invention targets exon 53 of the pre-mRNA of human dystrophin. In a known manner, the latter is made up of 212 bases or nucleotides and has the following sequence SEQ ID NO: 1:

```
ttgaaagaat tcagaatcag tgggatgaag tacaagaaca ccttcagaac cggaggcaac agttgaatga aatgttaaag gattcaacac aatggctgga agctaaggaa gaagctgagc aggtcttagg acaggccaga gccaagcttg agtcatggaa ggagggtccc tatacagtag atgcaatcca aaagaaaatc acagaaacca ag
```

Within the meaning of the invention, the regions described below are identified by the position of the nucleotides in reference to the sequence of exon 53 of the pre-mRNA of the dystrophin, i.e., sequence SEQ ID NO: 1.

In the rest of the description, the numbering used is therefore based on sequence SEQ ID NO: 1, with the understanding that the AON necessarily and by definition has a sequence complementary to that of its target. In practice, the sequence coding the AON, which is comprised in the vector of the invention, may for example be a sequence corresponding to the complementary reverse of the targeted region in exon 53 of the pre-mRNA of dystrophin. However, and as will be outlined below, AONs that only hybridize with a fragment of the targeted region, or hybridize with this region despite the presence of mismatches, are also capable of being effective. It must therefore be understood that the sequence coding the AON according to the invention comprises or consists of a sequence having at least a certain percentage of identity with the complementary sequence of the targeted region as defined within the meaning of the invention, or with the complementary sequence of at least one segment of this targeted region.

According to a first characteristic, the AON according to the invention targets the +30 to +69 region of exon 53 of the dystrophin pre-mRNA, namely the region with 40 bases with sequence:

g tacaagaaca ccttcagaac cggaggcaac agttgaatg

Preferably, the AON is directed against a segment of at least 33 bases (or nucleotides) of said region. In other words, the antisense hybridizes with at least 33 consecutive nucleotides of this region made up of 40 nucleotides.

Within the meaning of the invention, an oligonucleotide is said to hybridize with a target sequence when said oligonucleotide and the target sequence form, under determined moderate or advantageously high stringency conditions, a double-stranded pre-mRNA molecule.

The stringency conditions traditionally depend on experimental conditions such as the temperature, the ionic force, and the concentration in denaturing agents (such as formamide) in the reaction medium. These conditions and their possible variations are well known by those skilled in the art. Examples of high stringency conditions in particular include hybridization and washing operations done with compositions comprising sodium chloride (0.015 M) and sodium citrate (0.0015 M), at 65-68° C. (See Sambrook, Fritsch & Maniatis, Molecular Cloning. A Laboratory Manual, 2nd Ed, Cold Spring Harbor Laboratory, N Y 1989). Moderate stringency conditions may correspond to hybridization and washing operations done in these same compositions, but at a lower temperature, typically comprised between 50 and 65° C.

In other words, the oligonucleotide must be identical enough to the target sequence to allow matching of the two strands. This is provided once the two sequences are identical, but may also take place in the presence of one or more (in particular 2, 3, 4 or 5) divergent nucleotides, advantageously when the latter are located inside the sequence. In terms of identity, the oligonucleotide advantageously has at least 70%, 75%, 80%, 85% or even 90%, 91%, 92%, 93%, 94%, 95%, 96%, 97%, 98%, 99%, still more advantageously 100% identity with the targeted region. Thus, preferably, the sequence coding the AON according to the invention or said AON comprises or consists of a sequence having at least 70%, 75%, 80%, 85% or even 90%, 91%, 92%, 93%, 94%, 95%, 96%, 97%, 98%, 99%, still more advantageously 100% identity with the complementary sequence of the region going from nucleotides +30 to +69 of the sequence SEQ ID NO: 1.

According to one particular embodiment, the AON is directed against a segment with more than 33 bases, namely 34, 35, 36, 37, 38, 39 or even 40 bases of the region going from nucleotides +30 to +69 of the sequence SEQ ID NO: 1. According to one preferred embodiment, the oligonucleotide hybridizes with the entire +30 to +69 region of the sequence SEQ ID NO: 1. The term "hybridizes" is understood as defined above, i.e., covers the case of perfect identity between the oligonucleotide and the target region, but also cases where one or more mismatches exist. Thus, preferably, the sequence coding the AON according to the invention comprises or consists of a complementary sequence of the region going from the +30 to +69 nucleotides of the sequence SEQ ID NO: 1, or a complementary sequence of a segment with more than 33 bases, namely 34, 35, 36, 37, 38, 39 or even 40 bases of the region going from nucleotides +30 to +69 of the sequence SEQ ID NO: 1. Thus, preferably, the sequence coding the AON according to the invention or said AON comprises or consists of a sequence having at least 70%, 75%, 80%, 85% or even 90%, 91%, 92%, 93%, 94%, 95%, 96%, 97%, 98%, 99%, still more advantageously 100% identity with the complementary sequence of the targeted region, or with the complementary sequence of a segment with more than 33 bases, namely 34, 35, 36, 37, 38, 39 or even 40 bases of the region going from nucleotides +30 to +69 of the sequence SEQ ID NO: 1.

According to another embodiment, the AON can be directed against a region extending on either side of the targeted region. Thus, the AON coded by said sequence can hybridize with the region extending in 5' and/or 3' beyond the +30 to +69 region of exon 53, on the advantageous condition that such an AON has an efficacy, in terms of skipping exon 53, at least equal to that observed with an AON directed against a segment with more than 33 bases of the region going from nucleotides +30 to +69 of the sequence SEQ ID NO: 1, or even that of an AON directed against the region going from nucleotides +30 to +69 of the sequence SEQ ID NO: 1.

According to the invention, the size of the sequence coding the antisense oligonucleotide of interest is at least equal to the size of the segment targeted in exon 53, namely at least 33 nucleotides.

If the targeted segment has a larger size, which may in particular vary from 34 to 40 nucleotides, the sequence coding the AON according to the invention has a size that is at least equal, namely at least 34, 35, 36, 37, 38, 39 or even 40 bases. According to one particular embodiment, the sequence coding the AON according to the invention is made up of 34 bases, preferably 35, or even 36, 37, 38 or 39 bases. According to one favored embodiment, the sequence coding the AON according to the invention is made up of 40 nucleotides.

According to another particular embodiment, the sequence coding the AON implemented in the context of the invention has a size smaller than 70 bases, or even smaller than or equal to 65, 60, 55, 50 or even 45, 44, 43, 42 or 41 bases.

According to one particular embodiment, the sequence coding the antisense nucleotide, comprised in the AAVr of the invention, comprises or consists of the sequence SEQ ID NO:3 or SEQ ID NO: 4, advantageously SEQ ID NO: 3.

More specifically:
The sequence SEQ ID NO: 3 (which is referred to in the examples as "JR53" or "5902") corresponds to a sequence of 40 nucleotides coding an AON targeting the +30/+69 region of exon 53 of the pre-mRNA of dystrophin;
The sequence SEQ ID NO: 4 (which is referred to in the examples as "N3" or "5901") corresponds to a sequence of 33 nucleotides coding an AON targeting the +33/+65 region of exon 53 of the pre-mRNA of dystrophin.

According to one advantageous embodiment, said oligonucleotide is directed against the entire +30 to +69 region of exon 53 of the gene for dystrophin. Consequently, according to one particular embodiment, the sequence coding the AON comprised in the AAVr of the invention has a size of 40 bases and has the sequence SEQ ID NO: 3. Alternatively, it comprises the sequence SEQ ID NO: 3.

Characteristically according to the invention, the sequence coding the antisense oligonucleotide, or AON, is carried or conveyed by an AAVr vector. In other words, the sequence coding the antisense oligonucleotide, or AON, is contained or comprised in the AAVr genome.

The recombinant adeno-associated viral vectors (AAVr) are now recognized as high-performing tools for transferring genes, considered to treat many diseases. The AAVr vectors have a certain number of characteristics that make them suitable for gene therapy, in particular the absence of pathogenicity, a moderate immunogenic power and the ability to transduce post-mitotic cells and tissues stably and effectively. The expression of a particular gene conveyed by an AAVr vector may further be targeted in one or more cell types by appropriately choosing the serotype of the AAV, the promoter and the administration mode.

The AAVr are derived from the modification by genetic engineering of AAVs viruses. More than 100 natural serotypes of AAVs are now known. Many natural variants exist in the capsid for AAV, which has allowed the production and use of specific AAVrs with particularly appropriate properties for muscular dystrophy. AAVr vectors can be generated by using traditional molecular biology techniques, making it possible to optimize AAV viruses for the specific cellular delivery of nucleic acid molecules, to minimize the immunogenicity, to adjust the stability and lifetime of the particles, for effective degradation, and for transport at the nucleus level. As mentioned above, the use of AAVr is a typical method for delivering exogenous DNAs due to their non-toxicity, efficient DNA transfer and the possibility of optimizing them for specific purposes.

Among the serotypes for AAVs isolated from humans or nonhuman primates and that are well characterized, human serotype 2 is the first AAV that was used to produce AAVr vectors for gene transfer. Other AAV serotypes commonly used in AAVr vector production include AAV1, AAV3, AAV4, AAV5, AAV6, AAV7, AAV8, AAV9, AAV10, AAV11 and AAV12.

The viral genome for AAVs is made up of about 5000 nucleotides and comprises a gene coding for the regulating and replicating proteins (rep) and a gene coding for the structural proteins (cap). The sequences necessary in cis for the replication of the genome and its packaging are contained in a segment of 130 to 145 nucleotides found at each end of the genome (ITR for inverted terminal repeat).

From these viruses, a large number of recombinant vectors and chimeric (hybrid) AAVrs can also be produced and used.

Fragments of AAVs useful for assembly in vectors include the cap proteins, in particular vp1, vp2, vp3 and the hypervariable regions, the rep proteins, including rep 78, rep 68, rep 52 and rep 40, and the sequences coding these proteins. These fragments can be used in a wide variety of vectorial systems and host cells.

In the context of AAVr production, these fragments can be used alone, in combination with sequences and fragments of other AAV serotypes, in combination with elements of other AAVs or with viral sequences not derived from AAVs. In the context of the invention, appropriate AAVrs include, but are not limited to, modified AAVr comprising a non-natural capsid protein. Such an artificial capsid can be generated using any suitable technique, by using a selected AAV sequence (for example, a fragment of the vp1 capsid protein) in combination with heterologous sequences that can be obtained from a different selected AAV serotype, noncontiguous portions of the same AAV serotype, a non-AAV viral source or a non-viral source. An artificial AAV serotype may, without limitation, be a chimeric AAV capsid, a recombinant AAV capsid, or a "humanized" AAV capsid. Such examples of AAVs, or artificial AAVs, include AAV2/8 (U.S. Pat. No. 7,282,199), AAV2/5 (available from the National Institutes of Health), AAV2/9 (WO 2005/033321), AAV2/6 (U.S. Pat. No. 6,156,303), and AAVrh8 (WO 2003/042397), among others. According to one embodiment, the vectors useful in the compositions and methods of the invention contain at least sequences coding a capsid of a selected AAV serotype, for example an AAV8 capsid, or fragment thereof. According to another embodiment, useful vectors contain at least sequences coding a rep protein of a selected AAV serotype, for example an AAV8 rep protein, or fragment thereof. Optionally, such vectors contain both cap and rep proteins of AAV. In the vectors in which both rep and cap are present, the sequences of the AAV rep and cap proteins can originate from the same AAV, for example all coming from an AAV8. Alternatively, vectors can be used in which the rep sequences come from an AAV serotype different from that from which the cap sequences come. In one embodiment, the rep and cap sequences are expressed from separate sources (for example separate vectors, or a host cell and a vector). In another embodiment, these rep sequences are fused in phase with the cap sequences of an AAV having a different serotype to form a chimeric AAVr vector such as AAV2/8 (U.S. Pat. No. 7,282,199).

From AAVs, recombinant AAV genomes can be prepared, in which the genes coding for the viral proteins (rep and cap) are deleted, and only the two ITR repeated sequences remain. Producing recombinant vectors requires multiplying and packaging these recombinant genomes. This step is most often carried out in cells in culture that are transfected both with the recombinant genome of interest and plasmids coding for the missing rep and cap proteins (the cap proteins allowing the formation of the capsid). It is possible to use a recombinant genome and rep and cap genes coming from identical or different serotypes. Many combinations are thus possible.

If the serotypes are identical, only the serotype corresponding to the vector will be indicated. If the serotypes are different, so-called hybrid AAVr vectors are obtained, for which the serotypes used are indicated. As an example, an AAVr vector with serotype 2 is understood as being derived from a single serotype 2. Conversely, an AAVr vector with serotype 2/8 is a vector for which a recombinant genome is used derived from an AAV with serotype 2, while the genes coding for the used proteins of the capsid correspond to those of an AAV with serotype 8.

It has been shown that the capsid of AAV viruses, and consequently AAVr vectors, is generally associated with a particular cellular or tissular tropism.

According to the invention, the AAV implemented is advantageously based on an AAV with serotype 2 (AAV2), 8 (AAV8) or 9 (AAV9). In an appropriate manner, the capsid is chosen to allow effective, or even preferential transduction of the muscle, whether skeletal, cardiac or smooth. Thus and preferably, the AAV implemented is advantageously an AAV chosen from the following group: AAV2/1, AAV2, AAV2/6, AAV2/8, AAV2/9, AAV2/10. In a preferred manner, the vector is an AAV8 vector, still more advantageously an AAV2/8 vector.

Regarding the AAVr vectors implemented in the context of the invention, the AAV genome may be a single-stranded nucleic acid, a double-stranded nucleic acid, or a self-complementary nucleic acid.

The production of AAVr vectors is well known by those skilled in the art, and can be done by bi-transfection or tri-transfection of the HEK 293 cells, by the herpes simplex viral system or using the baculovirus system. Advantageously, the particles are obtained by bi- or tri-transfection of HEK 293 cells, or using the baculovirus system.

According to one particular embodiment, the vector according to the invention further contains or comprises a sequence coding a modified snRNA. More specifically, the sequence coding the antisense oligonucleotide (AON) according to the invention is introduced or inserted into the sequence coding the snRNA. In other words and preferably, the vector of the invention comprises a sequence coding an antisense oligonucleotide, which in turn is comprised in a sequence coding a modified snRNA. This embodiment allows the expression of an oligonucleotide comprising the modified snRNA in which the AON is integrated. As already stated, the integration of the AON within a modified snRNA results in stabilizing the expression of the resulting oligonucleotide, and further allowing a nuclear expression of these oligonucleotides.

The snRNA (for "small nuclear RNA") are small RNAs, present in the nucleus of the cells and involved in certain maturation steps of the messenger pre-RNA. They are called U1, U2, U3 . . . up to U13. It is well known that the native snRNA comprises a specific antisense region of the messenger pre-RNA whose maturation it provides. This sequence allows the hybridization with the target messenger pre-RNA. Furthermore, the region coding for the native snRNA (i.e., the sequence that is actually transcribed) in particular comprises a domain called sm, which codes for a binding site of the Sm protein (for "small nuclear ribonucleoprotein"). This domain is essential to the maturation activity of the pre-messenger RNAs of the snRNA (Grimm et al. *EMBO J.*, 1993, 12(3): 1229-1238). The region coding for the native snRNA further comprises a sequence coding for a stem-loop form for which it has been shown that it stabilizes the interaction between the snRNA and the pre-mRNA to be matured, thereby facilitating splicing (Sharma et al., *Genes Dev.*, 2014, 28(22): 2518-2531).

In the context of the invention, "sequence coding a modified snRNA" refers to an oligonucleotide having for sequence the native sequence of the functional gene of the snRNA, in which the sequences involved in the initial function of the snRNA are deactivated and/or modified, advantageously by insertion of the sequence coding the AON according to the invention. Within the meaning of the present invention, "native sequence of the functional gene" refers to the part of the endogenous gene comprising the region coding for the snRNA (i.e., the transcribed sequence), as well as the 5' and 3' regulator regions, and in particular the native promoter of the snRNA.

Preferably, the sequence coding for the modified snRNA codes an snRNA of type U7. According to this embodiment, the sequence of the binding sites of the Sm proteins is modified so as to deactivate the maturation of the pre-messenger RNAs coding the histones, advantageously by insertion of the sequence coding the AON according to the invention.

As described in relation to the snRNA of type U7, the sequence of the binding sites of the Sm proteins may further be modified so as to increase the nuclear concentration in snRNA, for example replaced by an optimized sequence, advantageously the smOPT sequence described by Schümperli et Pillai (*Cell. Mol. Life Sci.* 60: 2560-2570, 2004).

Conversely, and in order to facilitate the desired splicing, the sequence coding for the stem-loop form is preferably native. In other words, it is advantageously not modified.

As already stated, the modified snRNA implemented in the context of the invention preferably has no specific native antisense sequence targeting the messenger pre-RNA targeted by this snRNA, in the case at hand that of the histones for U7snRNA. Advantageously, this sequence is replaced by a sequence coding for the antisense oligonucleotide of interest, in the case at hand targeting the region comprised between the +30 and +69 bases of exon 53 of the pre-mRNA of the dystrophin.

Within the meaning of the invention, the sequence coding the modified snRNA may further be modified so as to replace the native sequence of the promoter of the snRNA with the sequence of another promoter, for example the sequence of the promoter of another type of snRNA. As an example and according to the invention, a "sequence coding a modified snRNA of type U7" refers to a sequence coding a snRNA of type U7 having undergone the modifications set out above, but comprising the native promoter of the snRNA U7. It is possible to replace this promoter with that of another snRNA, for example of type U1, U2 or U3, or with any other promoter appropriate for carrying out the invention. Various snRNA promoters are well known and have in particular been described by Hernadez (*J Biol Chem.*; 2001, 276(29):26733-6).

In the context of the invention and among the different types of snRNA, that of type U7 (U7snRNA), normally involved in the maturation of pre-messenger RNAs coding the histones, is preferably used.

In this context, it has further been shown that a particular domain, called "kiss domain," makes it possible, when it is fused with the antisense oligonucleotide carried by the snRNA, to hybridize with the stem-loop form of the snRNA. This hybridization causes a modification of the secondary structure of the modified snRNA that improves its interaction with the molecular machinery necessary for splicing. This domain has in particular been described in application WO 2011/113889, the contents of which must be considered to be part of this application. It is thus possible to integrate, into the sequence coding the modified snRNA according to the invention, a sequence coding for the "kiss domain" as described in this document.

In practice, these various modifications can be introduced into the sequences coding the snRNA using standard techniques in genetic engineering, such as PCR-directed mutagenesis.

It should be noted that the snRNA sequences are highly preserved between the different species. Thus, the sequence coding the modified snRNA used in the vector according to the invention can be of human or murine origin. Preferably, the sequence coding the modified snRNA used in the invention is of murine origin.

A typical construction according to the invention, coding an snRNA into which the sequence coding the AON of interest is inserted, advantageously comprises:

The non-translated 5' region of the gene coding the U7 snRNA, in particular comprising the promoter, advantageously of murine origin, as for example illustrated by nucleotides 1 to 258 of the sequence SEQ ID NO: 2;

The sequence coding the AON directed against the +30 to +69 region of exon 53 of the pre-mRNA of the dystrophin. As an example, nucleotides 259 to 298 of the sequence SEQ ID NO: 2 illustrate such a sequence, which codes an oligonucleotide with 40 bases (designated JR53 in the examples) and with sequence SEQ ID NO: 3. However, this antisense sequence may for example be replaced by the sequence SEQ ID NO: 4;

The modified binding sequence of the Sm protein, for example the smOPT sequence, corresponding to nucleotides 299 to 309 of the sequence SEQ ID NO: 2;

The sequence coding for the stem-loop form, unmodified and advantageously of murine origin, corresponding to nucleotides 310 to 340 of the sequence SEQ ID NO: 2;

The non-translated 3' region of the U7 snRNA, advantageously of murine origin, as for example illustrated by nucleotides 341 to 442 of the sequence SEQ ID NO: 2.

Preferably, the sequence coding for an antisense oligonucleotide of interest is integrated upstream from the modified binding sequence of the Sm protein, namely upstream from the smOPT sequence.

A modified snRNA as described above, advantageously of type U7, and integrating an anti-sense oligonucleotide of interest within the meaning of the invention, may for example have the sequence SEQ ID NO: 2.

It should be noted that other sequences may be integrated into the construction described above. In particular, other sequences can be integrated into the modified snRNA bearing the sequence coding the AON of interest, advantageously upstream or downstream from said sequence. It may in particular be considered to insert at least one sequence coding another AON of interest, directed against another region of exon 53 or allowing the skipping of another exon of the dystrophin, the skipping of which is also of interest.

The sequence coding the modified snRNA, carrying the sequence coding the AON of interest in the context of the invention, is advantageously inserted between the 2 ITR sequences of an AAV, for example of serotype 2. A corresponding construction is for example illustrated in sequence SEQ ID NO: 10.

It should be noted that in light of the size of the constructions considered in the context of the invention and the AAV packaging capacity, it is possible to consider integrating other constructions between the two ITR sequences of the AAVr vector according to the invention:

the introduction of one or more additional copies (for example from 1 to 9, advantageously from 1 to 3) of the sequence coding the construction according to the invention (snRNA in which the sequence coding the AON of interest is introduced), for example of sequence SEQ ID NO: 2;

the introduction of one or more other sequences coding a modified snRNA, carrying at least one sequence coding another AON of interest, directed against another region of exon 53 or allowing the skipping of another exon of the dystrophin, the skipping of which is also of interest.

In other words and in order to improve the exon skipping, the AAVr vector according to the invention may comprise several sequences coding for antisense oligonucleotides. Different embodiments can be considered, which are not mutually exclusive. According to a first embodiment, the AAVr vector comprises several modified snRNAs, each of these snRNAs comprising a sequence coding for an antisense oligonucleotide. According to a second embodiment, the AAVr vector comprises a single modified snRNA, which comprises several sequences coding for one or more antisense oligonucleotides. In this embodiment, it is understood that the AAVr may comprise several sequences coding for a same antisense oligonucleotide, and/or sequences coding for different anti-sense oligonucleotides.

The invention also encompasses any type of isolated cell, transduced by the AAVr vector described above. It advantageously involves muscle cells, in particular such as muscle fibers (myotubes) or muscle precursors (myoblasts). According to one particular embodiment, human embryo cells having required the destruction of a human embryo are excluded from the scope.

An isolated muscle tissue or a nonhuman organism transduced by said vector are also comprised in the scope of the sought protection. Among nonhuman organisms, animals are preferred.

The present application describes, for the first time, a potential therapeutic application for the claimed vector. The present invention therefore also relates to pharmaceutical compositions comprising, as active ingredient, at least one AAVr vector as defined in this application, as well as the use of this vector as a medicinal drug.

According to another aspect, the present invention relates to a composition, advantageously a pharmaceutical composition or drug, comprising an AAVr vector as described above, and potentially other active molecules (other gene therapy products, chemical entities, peptides, proteins, etc.), dedicated to treating the same disease or another disease.

Thus, the present invention offers pharmaceutical compositions comprising a nucleic acid according to the invention, in the case at hand an AAVr vector according to the invention. Such a composition comprises a therapeutically effective quantity of the vector according to the invention and a pharmaceutically acceptable and inert excipient. According to one particular embodiment, the expression "pharmaceutically acceptable" means approved by a federal or state regulatory authority, or listed in the American or European pharmacopeia, or any other pharmacopeia recognized as acceptable for humans and animals. The term "excipient" or "vehicle" refers to a diluent, adjuvant, carrier or support with which the therapeutic agent is administered. Such pharmaceutical excipients can be liquids, advantageously sterile, such as water and oils, including those of petroleum, animal, plant or synthetic origin, such as peanut oil, soy oil, mineral oil, sesame oil and the like. Water is a preferred excipient when the composition is administered intravenously. Saline solutions, aqueous dextrose, glycerol solutions can also be used as liquid excipients, in particular in the case of injectable solutions. Pharmaceutically acceptable excipients include starch, glucose, lactose, sucrose, sodium stearate, glycerol monostearate, talc, sodium chloride, glycerol, propylene glycol, water, ethanol and the like.

If necessary, the composition may also contain minor quantities of wetting or emulsifying agents, or pH buffer agents. These compositions may assume the form of solutions, suspensions, emulsions, extended-release formulations and the like. Examples of pharmaceutically acceptable excipients are for example described in "Remington's Pharmaceutical Sciences" by E. W. Martin. Such compositions contain a therapeutically effective quantity of the active ingredient, preferably in purified form, with an appropriate quantity of excipient so as to obtain the appropriate administration form for the patient.

According to one preferred embodiment, the composition is formulated in agreement with the typical procedures for pharmaceutical compositions appropriate for intravenous administration in humans. Traditionally, compositions for intravenous administration are solutions in an isotonic sterile aqueous buffer. If necessary, the composition may also contain a solubilizing agent and a local anesthetic such as lidocaine to ease pain at the injection site.

According to one embodiment, the composition according to the invention is suitable for administration in humans. The composition is preferably in liquid form, advantageously in the form of a saline composition, still more advantageously in the form of a composition containing a phosphate-buffered saline (PBS) or a solution of the Ringer-Lactate type.

The quantity of the therapeutic agent according to the invention, in the case at hand a recombinant vector, which is effective for treating dystrophic diseases, may be determined through standard clinical protocols. Furthermore, in vitro and/or in vivo tests can optionally be carried out to assist with the determination of the optimal dosage values. The precise dosage to be used in the composition may also depend on the selected administration route, the frequency of administration, the weight and/or the age of the patient, the severity of the disease, and must be decided upon by the practitioner in light of the particular context of each patient.

An appropriate administration mode must allow the delivery of a therapeutically effective quantity of the active ingredient to the target tissues, in particular to the skeletal muscles, and optionally to the heart and diaphragm. In the particular context of the invention, where the active ingredient is a recombinant AAV vector, the therapeutic dose is defined in terms of quantity of viral particles (vg for "viral genome") administered per kilogram (kg) of the patient.

The appropriate quantity must, in an appropriate manner, allow:
  The skipping of exon 53 for at least 10%, or even 20%, 30%, 40%, 50%, 60%, 70%, 80%, 90%, 95% or even 100% of the dystrophin transcripts. This can be evaluated using any technique known by those skilled in the art, for example by RT-PCR;
  The production of a truncated dystrophin (at least lacking the part coded by exon 53) representing at least 5%, or even 10%, 20%, 30%, 40%, 50%, 60%, 70%, 80%, 90%, 95% or even 100% of the dystrophin normally produced in a healthy organism. This can be evaluated using any technique known by those skilled in the art, for example by western blot.

In practice, and in particular in case of systemic administration, the composition is advantageously administered at a dose lower than or equal to $10^{15}$ vg/kg, or even $10^{14}$ vg/kg. It may be comprised between $10^{12}$ vg/kg and $10^{14}$ vg/kg, preferably comprised between $2.10^{12}$ vg/kg and $5.10^{13}$ vg/kg. In a known manner, as low a dose as possible making it possible to obtain a satisfactory result is encouraged so as in particular to avoid the problems of toxicity or immune reactions.

The available administration routes are topical (local), enteral (general effect, but delivery through the gastrointestinal (GI) tract), or parenteral (systemic action, but delivery through routes other than the GI tract). The preferred administration route for the composition according to the invention is the parenteral route and includes intramuscular administration (in the muscle) and systemic administration (in the circulatory system). In this context, the term "injection" (or perfusion) comprises intravascular administration, in particular intravenous (IV), and intramuscular (IM). Injections are generally done using a syringe or catheter.

According to one particular embodiment, the systemic delivery of the composition comprises the local administration of the composition at a treatment site, for example at a vein or artery of a weakened muscle. This administration technique, which involves a local administration that produces systemic effects, generally called loco-regional administration, has proven particularly appropriate to treat muscular pathologies. In practice, this may involve arterial or intravenous administration at one of the patient's limbs (leg or arm), done under pressure owing to the placement of a tourniquet, as for example described by Zheng et al. (Mol. Therapy, 2012, 20(2): 456-461), Toromanoff et al. (Mol. Therapy, 2008, 16(7): 1291-99) and Arruda et al. (Blood, 2010, 115(23): 4678-88).

Aside from loco-regional administration, one favored administration mode according to the invention is systemic administration. Systemic administration makes it possible to reach the entire body, and in particular all of the patient's muscles, including the heart and the diaphragm.

According to one favored embodiment, the systemic administration is done through injection of the composition into a blood vessel, namely via intravascular administration (intra-arterial or intravenous). In particular, the composition can be administered by intravenous injection, in a peripheral vein. Alternatively, the systemic administration can be an intramuscular injection.

In a manner known by those skilled in the art, the systemic administration is done under the following traditional conditions:
  A flow rate comprised between 1 and 10 mL/min, advantageously between 1 and 5 mL/min, for example 3 mL/min;
  A total injection volume comprised between 1 and 10 mL, preferably equal to 5 mL of the vectorial preparation per kg of the patient. The injected volume preferably must not represent more than 10% of the total blood volume, preferably about 6%.

A single administration of the composition according to the invention may prove sufficient. However, several administrations under different conditions can be considered, in particular:
  Repeated administration of the same vector by the same administration route;
  Administration of the same vector at different sites, in particular at different limbs;
  Administration of different recombinant vectors that may vary in terms of their serotype or the sequence coding the delivered AON.

According to one embodiment, the presence of the AAV vector according to the invention, and the associated beneficial therapeutic effects, are observed for at least 1 month, or 3 months, or 6 months, or 1 year, or 2 years, or 5 years or 10 years, or even for the entire lifetime of the patient.

As already stated, the patient is advantageously a human being, in particular a child, a teenager or a young adult. However, the therapeutic tool according to the invention can be appropriate and useful for treating other animals, in particular pigs and mice.

Such drugs are in particular intended to treat dystrophic diseases. In the context of the invention, a dystrophic disease refers to a disease related to a defect in the dystrophin gene. More specifically, it involves a defect for which skipping exon 53 makes it possible to reestablish the reading frame and the production of a dystrophin that is, granted, truncated, but is functional. Relative to the invention, a truncated, but functional dystrophin refers to a protein with a size smaller than the native protein, in particular not comprising the region coded by exon 53, but which is capable of performing at least some of the functions of the native protein, and in particular at least partially alleviating the symptoms associated with the absence of the native dystrophin, such as degeneration of the fibers, inflammation, necrosis, replacement of the muscle by scar or adipose tissue, muscle weakness, respiratory or heart failure, and premature death.

According to one particular embodiment, the dystrophic disease is Duchenne Muscular Dystrophy (DMD).

The forms of DMD are especially affected that are associated with deletions of exon 52 (Δ52), exons 50 to 52 (Δ50-52), exons 49 to 52 (Δ49-52), exons 48 to 52 (Δ48-52), exons 47 to 52 (Δ47-52), exons 46 to 52 (Δ46-52), exons 45 to 52 (Δ45-52), exons 43 to 52 (Δ43-52) and exons 10 to 52 (Δ10-52), or with a duplication of exon 53. The interest of the present invention is further illustrated relative to deletions Δ52 and Δ45-52, but also Δ48-52 and Δ50-52.

The nature of the deletions of the dystrophin gene present in a patient is easily determined by one skilled in the art, for example by sequencing or PCR.

In light of the remarkable effects observed on the restoration of dystrophin in muscle fibers affected by DMD, the invention also relates to the use of an AAVr vector as described above or a composition containing it to produce a medicinal drug, advantageously intended to treat dystrophic diseases, in particular DMD, particularly the forms listed above.

In other words, the present invention provides a method for treating dystrophic diseases, in particular as defined above, comprising the administration to a subject of such an AAV vector or a composition containing it.

EXAMPLES

The invention and resulting benefits will become clearer from the following examples, supported by the attached figures. In particular, the present invention is illustrated (example 1) relative to AAV 2/8 vectors comprising various sequences coding for the AON of interest within the meaning of the invention and a modified murine snRNA of type U7, tested on myoblasts having a deletion of exon 52 (Δ52) or exons 45-52 (Δ45-52) of the human gene for dystrophin. The invention is further illustrated (example 2) relative to an AAV 2/8 vector comprising a sequence coding a particular AON (JR53), and a modified murine snRNA of type U7, tested on myo-converted patient fibroblasts (fibromyoblasts) having a deletion of exon 52 (Δ52), or of exons 45-52 (Δ45-52), 48-52 (Δ48-52), or 50-52 (Δ50-52), of the human gene for dystrophin. These are not, however, in any way limiting, and their teaching may be extended to other AAV vectors, other modified snRNAs and subjects with Duchenne disease resulting from other mutations.

BRIEF DESCRIPTION OF THE DRAWINGS

FIG. 4A: Myoblasts Δ45-52 were transduced with vectors AAV2/8-U7-5901(denoted 01) or 5902 (denoted 02) or 5903 (denoted 03) or 5907 (denoted 07) or 5912 (denoted 12) or 5894 (denoted 94) or 5899 (denoted 99) (see Material and Methods) with a MOI of 300.10E+3. Their efficacy for skipping exon 53 was evaluated by nested RT-PCR. The total quantity of mRNA of the dystrophin is evaluated by RT-PCR Dys3-9, and the expression of housekeeping gene 18S makes it possible to evaluate the presence of mRNA.

FIG. 4B: Myoblasts Δ45-52 were transduced with vectors AAV2/8-U7-5901 or 5902 or 5903 or 5907 or 5912 or 5894 or 5899 (see Material and Methods) with a MOI of 300.10E+3. A multiplex western blot was done to detect the dystrophin and dysferlin proteins on the healthy subjects cells (8220; protein extract diluted to 1/5) and the non-infected DMD Δ45-52 cells (Non Inf). This figure is representative of 4 experiments done independently.

FIG. 5A: Myoblasts Δ52 were transduced with vectors AAV2/8-U7-5901 (denoted 01) or 5902 (denoted 02) or 5903 (denoted 03) or 5907 (denoted 07) or 5912 (denoted 12) or 5894 (denoted 94) or 5899 (denoted 99) (see Material and Methods) with a MOI of 300.10E+3. Their efficacy for skipping exon 53 was evaluated by nested RT-PCR. The total quantity of mRNA of the dystrophin was evaluated by RT-PCR Dys3-9, and the expression of housekeeping gene 18S makes it possible to evaluate the presence of mRNA.

FIG. 5B: Myoblasts Δ52 were transduced with vectors AAV2/8-U7-5901 or 5902 or 5903 or 5907 or 5912 or 5894 or 5899 (see Material and Methods) with a MOI of 300.10E+3. A multiplex western blot was done to detect the dystrophin and dysferlin proteins on the healthy subjects cells (8220; protein extract diluted to 1/5) and the non-infected DMD Δ52 cells (Ni). This figure is representative of 4 experiments done independently.

FIG. 6A: from left to right: molecular weight marker; healthy control myoblasts (hM); fibromyoblasts (hFM); noneligible DMD fibromyoblasts (FMstop16); cells of 3 DMD patients 5-13889 (FM13889 del49-52), 5-14211 (FM14211 del52), 5-14476 (FM14476 del45-52) with, for each patient, 4 conditions: fibroblasts (FH), fibromyoblasts not induced by doxycyclin (FM no), fibromyoblasts induced by doxycyclin (FM dox−), fibromyoblasts induced by doxycyclin and treated by JR53 (FM dox+); negative control of the reverse transcription without superscript enzyme (RT−), or without RNA (RTo); molecular weight marker.

FIG. 6B: identical to A with DMD patients DMD 5-14496 (FM14496 del45-52), 5-14498 (FM14498 del48-52), 5-14878 (FM14878 del50-52) and without the RTo control.

The RT-PCR products having the expected size without exon 53 are noted by an arrow.

Figure 7:
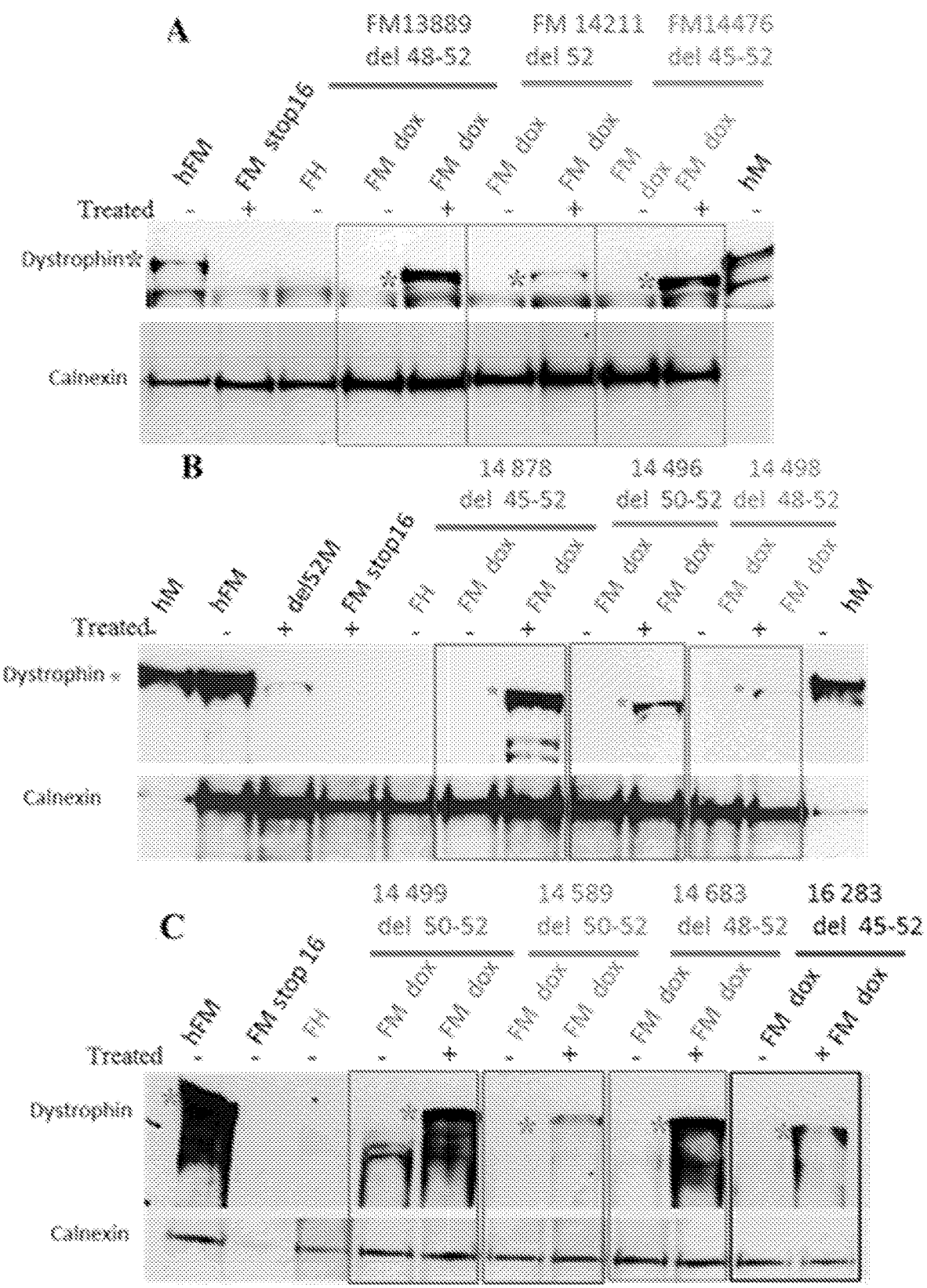

FIGS. 7A-7B: Expression of the dystrophin protein in the transduced human DMD fibromyoblasts revealed by Western blot.

The detection of the expression of dystrophin (top) and calnexin (bottom) was done by Western blot.

FIG. 7A: from left to right: healthy control fibromyoblasts (hFM); non-eligible DMD fibromyoblasts (FMstop16); DMD fibromyoblasts not induced by doxycyclin (FH); fibromyoblasts induced by doxycyclin for 3 DMD patients 5-13889 (FM13889 del48-52), 14211 (FM14211 del52), 5-14476 (FM14476 del45-52), each under 2 conditions: not treated with JR53 (FM dox−) and treated with JR53 (FM dox+); healthy myoblasts (hM).

FIG. 7B: identical to A with DMD patients DMD 5-14878 (FM14878 del45-52), 5-14496 (FM14496 del50-52), 5-14498 (FM14498 del48-52).

FIG. 7C: identical to A with DMD patients DMD 5-14499 (FM14499 del50-52), 5-14589 (FM14589 del50-52), 5-14683 (FM14683 del48-52), 5-16283 (FM16283 del45-52).

The efficacy of JR53 was tested in two or three experiments for each lot of DMD fibromyoblasts.

EXAMPLE 1: EFFICACY OF VECTORS COMPRISING SEQUENCES CODING FOR ANTISENSE OLIGONUCLEOTIDES (AON) IN SKIPPING EXON 53 OF DYSTROPHIN ON MYOBLASTS

The efficacy of the recombinant AAV8s described in more detail below was tested blind in the context of two parallel studies.

The first study (I) aimed to compare the efficacy of different antisense sequences at the skipping of exon 53 (evaluated by RT-PCR on the mRNA of the dystrophin), in qualitative and quantitative terms.

The second study (II) aimed to confirm the efficacy of different antisense sequences at the skipping of exon 53 (evaluated by RT-PCR on the mRNA of the dystrophin) and at the produced dystrophin protein.

A. Materials and Methods

1. Antisense, Vectors and Plasmids

The antisense sequences identified in Table 1 below were tested:

| Target region in exon 53 | Sequence of the antisense oligonucleotide (AON) | Name of the AON |
|---|---|---|
| (sequence without homology with exon 53) | SEQ ID NO: 9 | 5899 (scramble) |
| +33 to +59 | SEQ ID NO: 6 | 5894 (N1) |
| +36 to +59 | SEQ ID NO: 5 | 5907 (N2) |
| +33 to +65 | SEQ ID NO: 4 | 5901 (N3) |
| +36 to +65 | SEQ ID NO: 7 | 5903 (Di I) |
| +30 to +69 | SEQ ID NO: 3 | 5902 (JR53) |
| +45 to +62 and +128 to +145 | SEQ ID NO: 8 | 5912 (Dtex53) |

They were cloned by directed mutagenesis in the optimized murine U7snRNA gene containing its own promoter. The corresponding construction related to AON 5902 (JR53) is illustrated in sequence SEQ ID NO: 2.

The corresponding constructions have been inserted into an expression plasmid, for example the pFBD plasmid.

As described by Ayuso et al. (Hum. Gen. Ther., 2014, Nov. 25(11): 977-87), the plasmids used to produce AAV2/8 vectors are:
- pDP10 bearing the rep-2 and cap-8 genes and the auxiliary genes of the E2b, E4, VARNA adenovirus; and
- the vector plasmid bearing the corresponding ITR-2s and the transgene (constructions described above).

2. Production of AAV2/8 Vectors

The AAV8 vectors were produced from HEK293 cells (having stably integrated, in their cellular genome, the E1A and E1B genes) cultivated in an adherent system in 5 tray Cell Stack. The cells, cultivated in the DMEM medium containing 10% fetal calf serum (volume/volume) as well as penicillin and streptomycin (1% volume/volume for each antibiotic), were transfected using the precipitation technique with calcium phosphate for 2 plasmids (auxiliary plasmid: pEP10 carrying the rep-2 and cap-8 genes and the auxiliary genes of the E2b, E4, VARNA adenovirus and the vector plasmid carrying the corresponding ITR-2s and the transgene).

The medium was changed after transfection with the DMEM medium without serum. The AAVr particles were harvested after 72 H in the supernatant and precipitated with 40% polyethylene glycol plus benzonase. The particles were next purified on two successive CsCl gradients. The CsCl contaminations were eliminated by dialysis against dPBS 1× buffer. The particles were next frozen at −80° C. in low binding tubes (Ayuso et al., Hum. Gen. Ther., 2014, Nov. 25(11): 977-87).

3. Titration of the Vectors

The productions of vectors were treated with DNase to eliminate the contaminating free DNA, then viral nucleic acids were extracted. After extraction, the nucleic acids were diluted and the number of copies of AAV viral genomes (AAV/ITR amplicon) was determined by qPCR with a linearized and standardized plasmid line.

For the qPCR, the following primers and probe were used:

```
AAV18mers.R:
                                       (SEQ ID NO: 11)
GTAGATAAGTAGCATGGC AAV22mers.F:
                                       (SEQ ID NO: 12)
CTCCATCACTAGGGGTTCCTTG AAV_MGB.P:
                                       (SEQ ID NO: 13)
TAGTTAATGATTAACCC.
```

4. Immortalized Myoblast Lines

Two lines of Duchenne patients were used, one pertaining to a deletion in the dystrophin gene of exons 45 to 52 (Δ45-52) and the other of exon 52 (Δ52). A third line of healthy subject myoblasts served as a control (8220).

I. Protocol Implemented for Study I:

5. Transduction of the Immortalized Myoblasts by AAV2/8

The cells were seeded at 190,000 cells per well of a six-well plate, then cultivated in the proliferation medium (skeletal muscle cell basal medium+skeletal muscle cell growth medium kit, Promocell Ref: C23160). After about 24 hours, the cells were transduced at the MOIs of $1^{e}5$ and $5^{e}5$ vg/cell with the different U7snRNA recombinant AAV2/8 vectors modified blind and an AAV2/8 control allowing the expression of the Green fluorescent protein (GFP) in order to verify the efficacy of the transductions.

After 3 days of culture, the cells were harvested and the cell pellets were frozen dry at −80° C. The pellets were next used for DNA and RNA purifications.

6. Evaluation of the Number of Viral Genomes Per Cell

The AAV genomes were extracted using the Gentra Puregene kit (Qiagen).

The number of vector DNA copies was determined using the TaqMan Real time PCR procedure. The primers and probe were developed to amplify (i) the Inverted Terminal Repeats (ITRs) (see point 3) and (ii) the endogenous gene of the albumin. For each sample, the Ct values were compared to those obtained with different dilutions of a standard plasmid containing both ITRs and the albumin gene. The final results were expressed in viral genomes per diploid genome (vg/dg for viral genome/diploid genome).

```
Alb.F:
                                        (SEQ ID NO: 14)
GCTGTCATCTCTTGTGGGCTGT

AIb.R:
                                        (SEQ ID NO: 15)
ACTCATGGGAGCTGCTGGTTC

AlbVIC.P:
                                        (SEQ ID NO: 16)
CCTGTCATGCCCACACAAATCTCTCC
```

7. Evaluation of the Exon Skipping by Nested RT-PCR

The RNA extraction from the dry cell pellet was done with 1 mL of Trizol Reagent using the supplier's instructions (Life Technologies, Ref 15596-026). The RNA were recovered in 30 µL of sterile water, then treated by two successive DNase steps in order to eliminate the typical RNA contaminations by the viral DNA (Ambion, Ref. AM1907). 500 ng of RNA was used for the reverse transcription reaction (Life Technologies kit, Ref. 28025-013). During this step, reverse transcription negative controls were done on each sample in order to verify the absence of contamination by viral DNA.

To detect the exon skipping, a first PCR (PCR1) with the Gotaq G2 enzyme (Promega, Ref.: M7805) was done from 1 µL of complementary DNA (cDNA) in a final volume of 50 µL with the appropriate pairs of primers of each cell type (see the list of primers below) for 25 cycles [95° C. 30 seconds-50° C. or 58° C. 1 min-72° C. 2 min], then 1 µL of PCR1, in a volume of 50 µL total, was re-amplified (PCR2) for 30 cycles [95° C. 30 seconds-50° C. or 58° C. 1 min-72° C. 2 min] with a second pair of primers inside the PCR1 product. The nested PCR products were analyzed by electrophoresis on 1.5% agarose gel in Tris-acetate-EDTA buffer. The bands corresponding to the exon skipping were cut, purified through a column, using the Nucleospin Gel and PCR Clean-up kit (MACHEREY-NAGEL, Ref: 740609.250) and sequenced.

The pairs of primers used for exon 53 skipping were:
For the DMD Δ52 line:
 PCR1: ex51 hDMD Fext and ex54 hDMD Rext at 50° C.
 PCR2: ex51 hDMD Fint and ex54 hDMD Rint at 50° C.
For the Δ45-52 line:
 PCR1 Dys43F/Dys57R at 58° C.
 PCR2 Dys44F/Dys56R at 58° C.
Sequences of Primers for Exon 53 Skipping:

```
ex51 hDMD Fext:
                                        (SEQ ID NO: 17)
GTTACTCTGGTGACACAACC ex54 hDMD Rext:
                                        (SEQ ID NO: 18)
ATGTGGACTTTTCTGGTATC ex51 hDMD Fint:
                                        (SEQ ID NO: 19)
ACTAGAAATGCCATCTTCCT ex54 hDMD Rint:
                                        (SEQ ID NO: 20)
CAAGTCATTTGCCACATCTA Dys43-F:
                                        (SEQ ID NO: 21)
CCTGTGGAAAGGGTGAAGC Dys44-F:
                                        (SEQ ID NO: 22)
CGATTTGACAGATCTGTTGAG Dys56-R:
                                        (SEQ ID NO: 23)
TGAGAGACTTTTTCCGAAGT Dys57-R:
                                        (SEQ ID NO: 24)
AAGTTCCTGCAGAGAAAGGT
```

The expected sizes for the PCR2 are indicated in Table 2 below.

| Cells | Primers | Size of the amplicon containing exon 53 | Size of the amplicon not containing exon 53 |
|---|---|---|---|
| Δ52 | ex51 hDMD Fint ex54 hDMD Rint | 438 bp | 226 bp |
| Δ45-52 | Dys44-F Dys56-R | 870 bp | 658 bp |

8. Quantification of the Exon 53 Skipping by Quantitative PCR in the Δ45-52 Line Two RTqPCR were done in order to quantify the skipping of exon 53. The first is specific to the transcript no longer containing exon 53 for dystrophin (RTqPCR of the junction of exons 44 and 54). The second was used to normalize, by amplifying all of the transcripts of the dystrophin (RTqPCR of the junction of exons 4 and 5). The cDNAs derived from the reverse transcription reaction were diluted, then amplified using the Premix Ex Taq kit using the Taqman technology according to the supplier's recommendations (Takara, Ref. RR390w) with 0.3 µmol/L of each primer, and 0.25 µmol/L of the Taqman probe (see the list of primers and probes below) for 40 cycles [95° C. 15 seconds-57° C. 1 min]. To validate the efficacy of the RTqPCR and to quantify the transcripts, dilution lines of a reference plasmid containing the sequences of interest were deposited in parallel with the samples on the plate.

For the dystrophin RTqPCR without exon 53, the following primers and probe are used:

hDys-44/54-F:
(SEQ ID NO: 25)
CCTGAGAATTGGGAACATGCTAA hDys-44/54-R:
(SEQ ID NO: 26)
GCCACTGGCGGAGGTCTT hDys-44/54-P:
(SEQ ID NO: 27)
GGTATCTTAAGCAGTTGGC = Taqman
probe straddling the junction of exons 44 and 54

For the total dystrophin RTqPCR, the following primers and probe are used:

hDys-4/5-F:
(SEQ ID NO: 28)
CATGCCCTGAACAATGTCAACAAG hDys-4/5-R:
(SEQ ID NO: 29)
TCCATCTACGATGTCAGTACTTCCA hDys-4/5-P:
(SEQ ID NO: 30)
TTGCAGAACAATAATGTTGATTTA = Taqman
probe straddling the junction of exons 4 and 5

II. Protocol Implemented for Study II:
5. Transduction of the Immortalized Myoblasts by AAV2/8

The cells were seeded at 100,000 cells per 35 mm well, then cultivated in the aforementioned proliferation medium until 80% confluence. After about 24 hours, the cells were infected with the different recombinant AAV2/8 vectors at the MOI of 250,000 vg/cell in a differentiation medium (IMDM without serum with gentamycin), at 37° C.

After 4 h to 6 h, 250 μL of IMDM doped with gentamycin was added. After 9 days of culture in the differentiation medium, a sample of the culture medium of 1/10 of the volume of the 35 mm well is withdrawn. It was next be used for the RNA purification for RT-PCR analyses. In parallel, the cells were scraped, rinsed and centrifuged for 1 minute at 11,000 g or 5 minutes at 1500 rpm. The pellets were frozen dry at −80° C. The pellets are next used for DNA purification and viral genome quantification.

6. Evaluation of the Number of Viral Genomes Per Cell
See point I-6 above.
7. Evaluation of the Exon Skipping by Nested RT-PCR In order to conduct the nested RT-PCR, the RNA was extracted through a column using the Nucleospin RNAII kit and eluted in 30 μL of water (DNase/RNase free). 500 ng of RNA was used for the reverse transcription reaction (Superscript II Life Technologies kit, Ref. 18064-014).

For the detection of exon skipping, a 1st PCR was done on 2 μL of cDNA and a total volume of 20 μL with the appropriate pairs of primers for each cell type (see list below) for 30 cycles [95° C. 30"-56° C. 1'-72° C. 2'], then 3 μL of PCR1, in a total volume of 30 μL, were amplified for 25 cycles with a second pair of primers inside the PCR1 product. Regarding the 18S and PO RNA analysis, only 1 PCR was done. The nested PCR products were anlyzed electrophoresis on 1.8% agarose gel in Tris-acetate-EDTA buffer. The bands corresponding to the exon skipping were cut, purified through a column, using the Nucleospin Gel and PCR Clean-up kit (MACHEREY-NAGEL, Ref: 740609.250) and sequenced (by GATC).

The pairs of primers used for exon 53 skipping were:
For the Control Myoblasts Wt (8220) and DMD Δ52:
PCR1: Dys49F/Dys57R
PCR2: Dys50F/Dys56R (human dystrophin)
For Myoblasts Δ45-52:
PCR1 Dys43F/Dys57R
PCR2 Dys44F/Dys56R (human dystrophin)
Sequences of 5'->3' Primers for Exon 53 Skipping:

Dys43-F:
(SEQ ID NO: 21)
CCTGTGGAAAGGGTGAAGC

Dys44-F:
(SEQ ID NO: 22)
CGATTTGACAGATCTGTTGAG

Dys49-F:
(SEQ ID NO: 31)
CAACCGGATGTGGAAGAGAT

Dys50-F:
(SEQ ID NO: 32)
CTCTGAGTGGAAGGCGGTAA

Dys56-R:
(SEQ ID NO: 23)
TGAGAGACTTTTTCCGAA-GT

Dys57-R:
(SEQ ID NO: 24)
AAGTTCCTGCAGAGAAAG-GT

Sequences of Other Primers for 18S, PO and Total Human Dystrophin:

PO-F:
(SEQ ID NO: 33)
GGCGAGCTGGAAGTGCAACT

PO-R:
(SEQ ID NO: 34)
CCATCAGCACCACAGCCTTC

18S-F:
(SEQ ID NO: 35)
TCAAGAACGAAAGTCGGAGGTTCG

18S-R:
(SEQ ID NO: 36)
TTATGCTCAATCTCGGGTGGCTG

Dys3-F:
(SEQ ID NO: 37)
GAGAACCTCTTCAGTGACCTAC

Dys9-R:
(SEQ ID NO: 38)
GAGGTGGTGACATAAGCAGC

The primers used for each cell type and the expected sizes are indicated in Table 3 below.

| Cells | Primers | Parental band size (amplicon with exon 53) | Expected band size (Amplicon without exon 53) |
|---|---|---|---|
| 8220 Control | Dys43-F-Dys57-R Dys44-F-Dys56-R | 2010 bp | 1888 bp |
| Δ45-52 | Dys43-F-Dys57-R Dys44-F-Dys56-R | 870 bp | 658 bp |

| Cells | Primers | Parental band size (amplicon with exon 53) | Expected band size (Amplicon without exon 53) |
|---|---|---|---|
| Δ52 | Dys49-F-Dys57-R Dys50-F-Dys56-R | 1065 bp | 853 bp |

8. Evaluation of the Restoration of the Expression of the Dystrophin by Multiplex Western Blot The proteins were extracted from transduced and differentiated cells for 9 days (see paragraph 5) in a buffer containing 125 mM of sucrose, 5 mM of Tris-HCl pH 6.4, 6% of XT-Tricine migration buffer (Bio-Rad), 10% of SDS, 10% of glycerol, 5% of 13-mercaptoethanol and antiproteases. The samples were denatured for 5 minutes at 95° C., then pretreated with the Compat-Able™ Protein Assay preparation Reagent Set kit (Thermo Scientific Pierce). The concentration of the proteins was determined by the BCA Protein Assay Kit (Thermo Scientific Pierce). 75 µg of proteins were deposited on a Criterion XT Tris-Acetate 3-8% pre-poured gel (Bio-Rad). The dystrophin was detected by hybridization of the membrane with the NCL-DYS1 monoclonal primary antibody (Novocastra) diluted to 1:50 followed by an incubation with the anti-mouse sheep secondary antibody (HRP), diluted to 1:15,000. The proteins were revealed by the SuperSignal West Pico Chemiluminescent Substrate kit (Thermo Scientific Pierce).

B. Results and Discussion

A double-blind study was conducted with the candidate antisense sequences, inserted into the optimized murine U7snRNA gene and containing its own promoter, carried by the AAV2/8s, on two lines of immortalized human myoblasts, Δ45-52 and Δ52, respectively.

The tested vectors and their titer are indicated in Table 4 below:

| Vector | Titer (vg/mL) (qPCR ITR-G) |
|---|---|
| rAAV2/8-U7-#5899 | $1.20^{+12}$ |
| rAAV2/-U7-#5894 | $7.54^{+11}$ |
| rAAV2/8-U7-#5907 | $2.70^{+12}$ |
| rAAV2/8-U7-#5901 | $2.00^{+12}$ |
| rAAV2/8-U7 #5903 | $1.85^{+12}$ |
| rAAV2/8-U7-#5902 | $9.60^{+11}$ |
| rAAV2/8-U7 #5912 | $3.10^{+12}$ |
| rAAV2/8 GFP | $1.14^{+12}$ |

I. Results of Study I

These vectors were tested at a MOI of $1^e5$ and $5^e5$ vg/cell under proliferation conditions blind by two handlers. The efficacy of the transductions was estimated by flux cytometry and was between 68% and 96% of the transduced cells.

As shown in Table 5 below, the quantification by qPCR of viral genomes per cell shows the homogeneity of transduction of the different vectors:

| Line | Vector | MOI | VG/DG |
|---|---|---|---|
| Δ45/52 | NT | / | 0.003 |
|  | GFP | 1E+05 | 844 |
|  |  | 5E+05 | 3,416 |
|  | 5894 | 1E+05 | 618 |
|  |  | 5E+05 | 3,266 |
|  | 5899 | 1E+05 | 716 |
|  |  | 5E+05 | 3,081 |
|  | 5901 | 1E+05 | 1,367 |
|  |  | 5E+05 | 5,832 |
|  | 5902 | 1E+05 | 979 |
|  |  | 5E+05 | 16,103 |
|  | 5903 | 1E+05 | 1,304 |
|  |  | 5E+05 | 5,592 |
|  | 5907 | 1E+05 | 321 |
|  |  | 5E+05 | 2,978 |
|  | 5912 | 1E+05 | 554 |
|  |  | 5E+05 | 2,663 |
| Δ52 | NT | / | 0.006 |
|  | GFP | 1E+05 | 2,925 |
|  |  | 5E+05 | 16,057 |
|  | 5894 | 1E+05 | 3,373 |
|  |  | 5E+05 | 17,311 |
|  | 5899 | 1E+05 | 2,474 |
|  |  | 5E+05 | 16,950 |
|  | 5901 | 1E+05 | 2,697 |
|  |  | 5E+05 | 24,826 |
|  | 5902 | 1E+05 | 4,118 |
|  |  | 5E+05 | 37,806 |
|  | 5903 | 1E+05 | 2,628 |
|  |  | 5E+05 | 24,201 |
|  | 5907 | 1E+05 | 1,557 |
|  |  | 5E+05 | 10,808 |
|  | 5912 | 1E+05 | 1,915 |
|  |  | 5E+05 | 10,264 |

Figure 1:
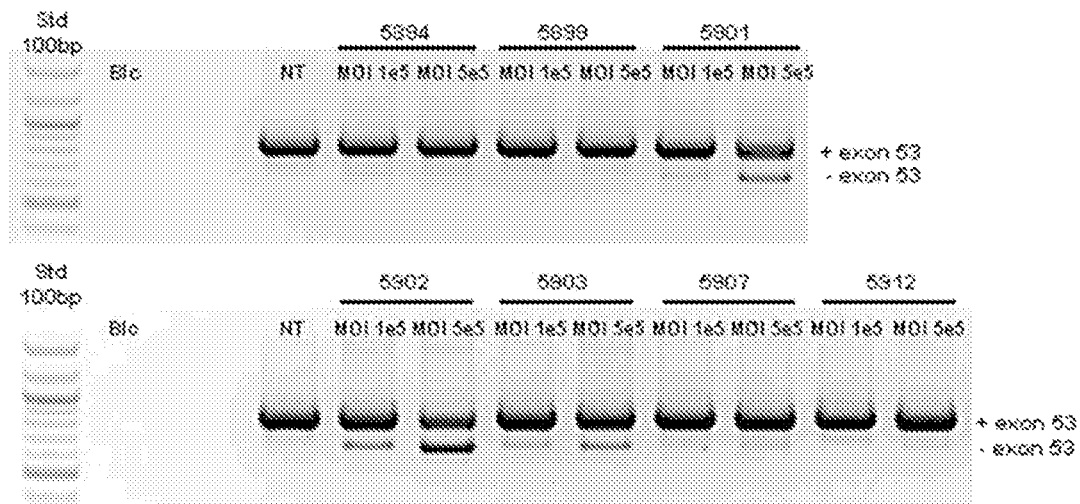
FIG. 1: Evaluation of skipping exon 53 of the human dystrophin messenger after transduction of myoblasts Δ45/52 with the different rAAV8 vectors tested blind. The analysis was done by nested RT-PCR between exons 44 to 56. Blc: PCR water control; NT: cells not transduced.
Figure 2:
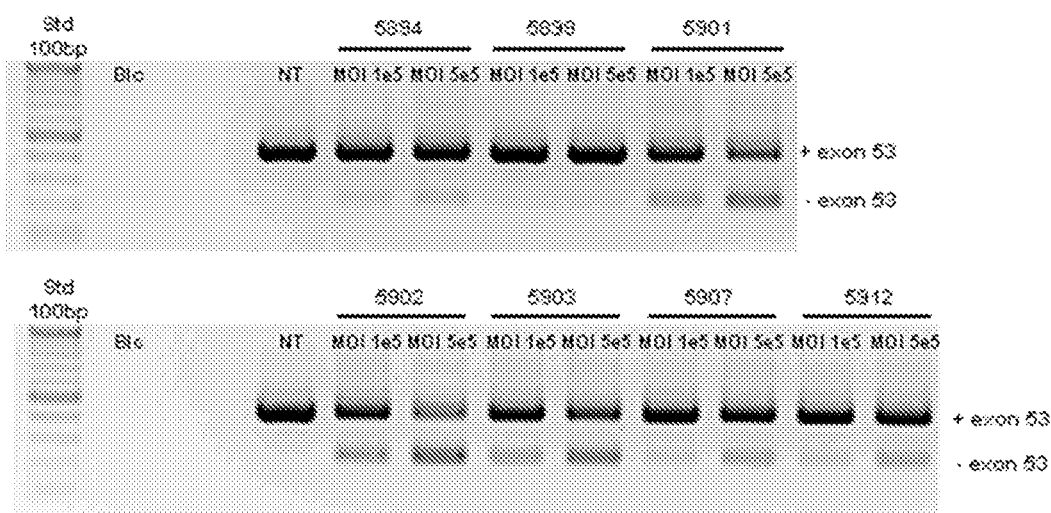
FIG. 2: Evaluation of skipping exon 53 of the human dystrophin messenger after transduction of myoblasts Δ52 with the different rAAV8 vectors tested blind. The analysis was done by nested RT-PCR between exons 51 to 54. Blc: PCR water control; NT: cells not transduced.
Figure 3:
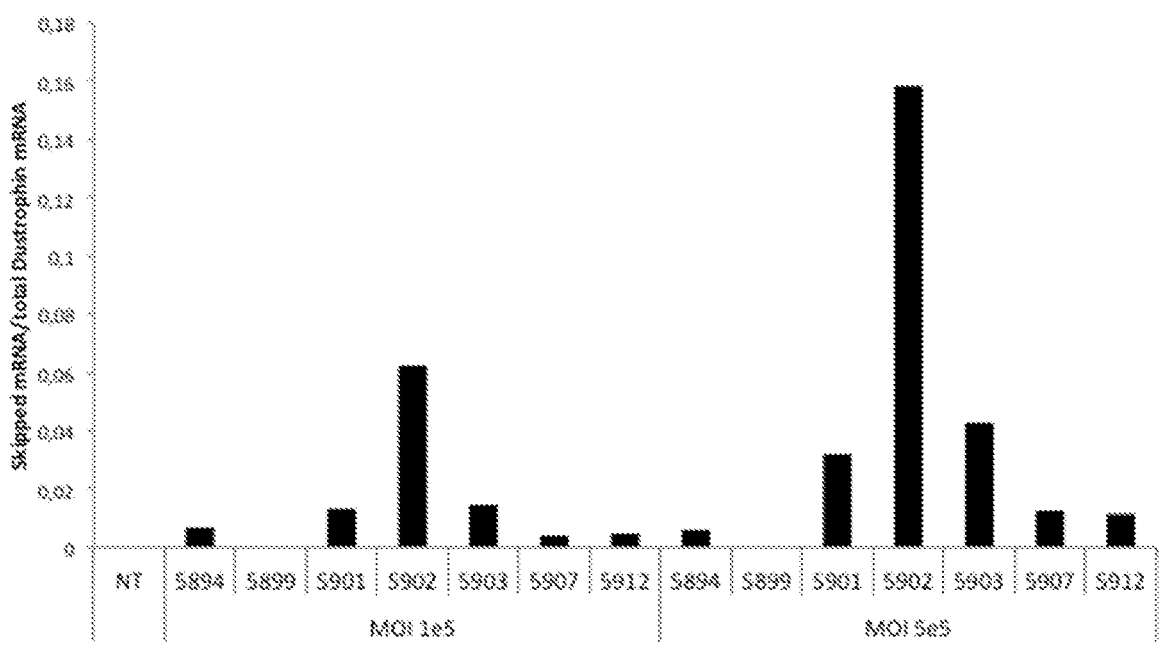
FIG. 3: Evaluation by RTqPCR of the expression level of the messenger for human dystrophin without exon 53 (based on the messenger level of the total dystrophin) after transduction of myoblasts Δ45/52 with the different rAAV8 vectors tested blind. NT: cells not transduced.

FIGS. 1 to 3 show the results of the evaluation of the efficacy of the constructions after transduction of the DMD Δ45-52 and Δ52 myoblasts, respectively: FIGS. 1 and 2 make it possible to assess the skipping of exon 53 by nested RT-PCR on the two cell lines and FIG. 3 shows the quantification of this skipping by RTqPCR on line Δ45-52.

II. Results of Study II

These vectors were tested at a MOI of 300.E+3. The transduced cells were differentiated for 9 days in order to obtain the differentiation conditions making it possible to show a restoration of the dystrophin protein in the corrected cells (see Material and Methods).

Figure 4:
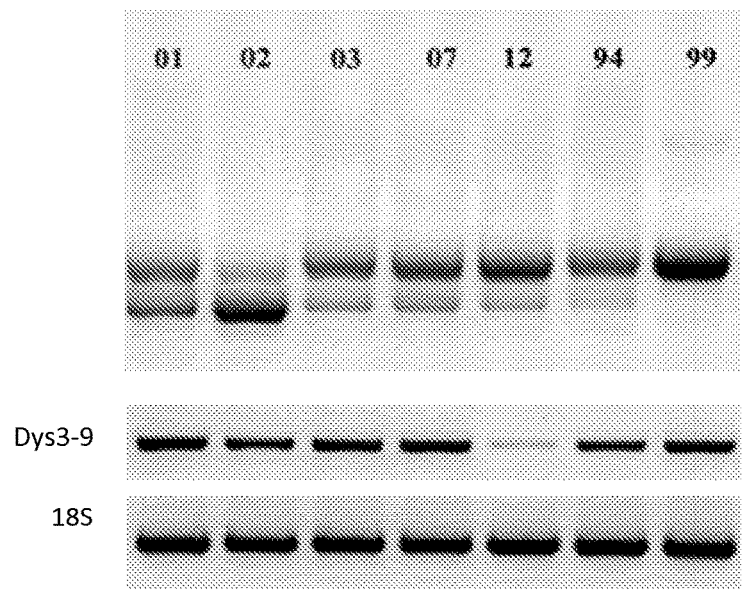
FIGS. 4A-4B: Skipping exon 53 of the pre-mRNA for human dystrophin on DMD myoblasts Δ45-52.
Figure 4:
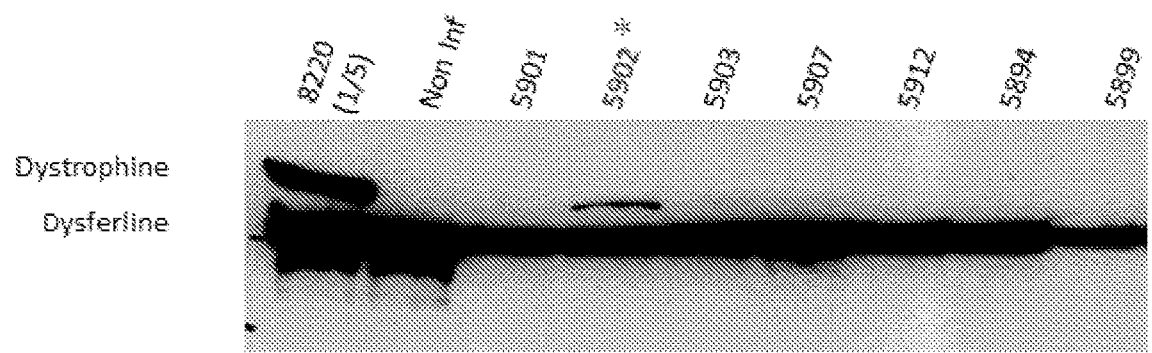
Figure 5:
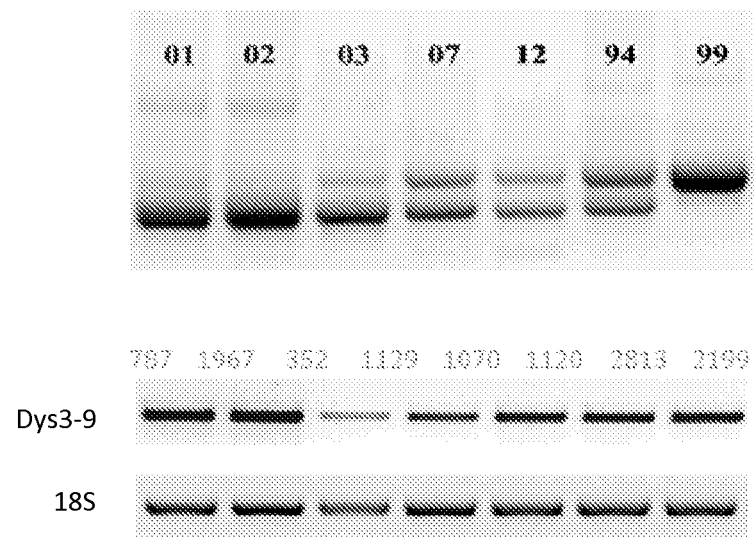
FIGS. 5A-5B: Skipping exon 53 of the pre-mRNA for human dystrophin on DMD myoblasts Δ52.
Figure 5:
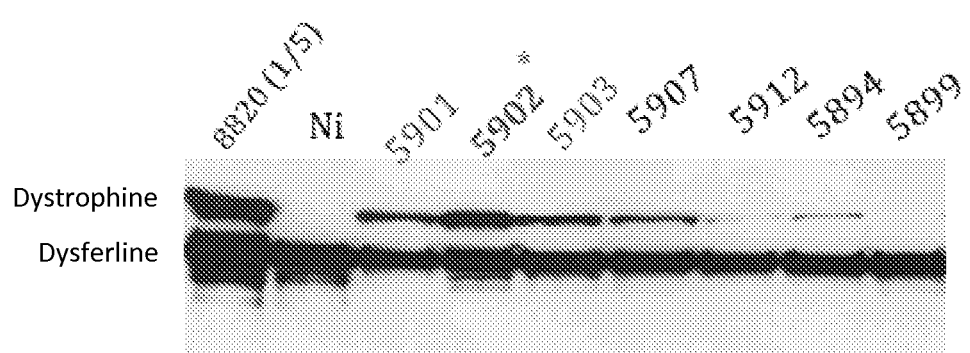

FIGS. 4 and 5 show the results of the evaluation of the efficacy of the constructions after transduction of the DMD Δ45-52 and Δ52 myoblasts, respectively.

FIGS. 4A and 5A make it possible to assess the skipping of exon 53 by nested RT-PCR and FIGS. 4B and 5B show the results of the study of the expression of the dystrophin protein by Western blot.

Conclusions

These two independent and completely consistent studies show that the results of the efficacy of the exon skipping are identical for the two DMD lines, namely efficacy of the following magnitude: 5902>5901=5903. Likewise, on the two lines of myoblasts, the construction that carries the AON 5902 is the most effective to restore the expression of the dystrophin.

The antisense sequences cloned in U7 and vectorized in AAV2/8, in particular the sequences called JR53 (SEQ ID NO: 3) and N3 (SEQ ID NO: 4), are all more effective than the Dtex53 sequence according to the prior art (5912).

EXAMPLE 2: EFFICACY OF VECTORS COMPRISING THE JR53 SEQUENCE (SEQ ID NO: 3) IN THE SKIPPING OF EXON 53 OF DYSTROPHIN, ON HUMAN FIBROMYOBLASTS

A. Materials and Methods

1. Cell Culture

The fibroblasts of DMD patients were cultivated in an IMDM (Iscove's Modified Dubelco Medium) culture medium (Life Technologies) doped with 10% of fetal calf serum (FCS) and 10 µg/mL of gentamycin. At confluence, the cells were separated in a trypsin/EDTA solution and amplified. For each patient, samples were prepared and stored cold (cryo-conservation).

2. Myoconversion: Conversion of the Human DMD Fibroblasts into Fibromyoblasts 2.1. Vector Used for the Myo-Conversion The myo-conversion technique and the tools allowing it to be carried out, in particular the appropriate lentiviral vectors, are known by those skilled in the art and for example described in Cooper et al. (Neuromuscular Disorders 17 (2007), 276-284) and Chaouch et al. (Human Gene Therapy 20 (2009), 784-790).

The vector used for the myo-conversion was the GU007HT_psin_pTRE_MyoD_hPGK_rtTA2M2 lentiviral vector, produced by Gënëthon (lot no. 13RO281 GU 007H), also subsequently called LV/MyoD or LV/MyoDi.

2.2. Myo-Conversion Method

The human fibroblasts (HF) were separated with a trypsin/EDTA solution, centrifuged for 5 minutes at 300 g, returned to suspension in DMEM (High glucose Dulbecco's Medium) and counted. 25,000 cells were transferred into an Eppendorf tube with 5 µL of LV/MyoDi in DMEM without antibiotic, in a total volume of 100 µL, then incubated for 30 minutes at 37° C. (mixed 2 or 3 times). Next, the mixture (cells +vector) contained in each tube was seeded in a 22 mm well (P12) containing 900 µL of DMEM, 10% FCS, 100 µL/mL of penicillin, 100 µg/mL of streptomycin, and placed in an incubator at 37° C., 5% $CO_2$ for 3 days. From the third day, the medium was completely replaced to eliminate the viral particles. The cells transduced by LV/MyoDi were next amplified and frozen at −80° C. before being transferred into liquid nitrogen.

2.3. Validation of the Efficacy of the Myo-Conversion by Immunocellular Marking of MyoD1

The fibromyoblasts (FM) were inoculated on a 22 mm strip on matrigel at 10,000 cells/well. The myo-conversion was induced after 24 hours by adding 10 µg/mL of doxycyclin for 4 to 6 days in a proliferation medium. The fibromyoblasts were fixed with 2% of para-formaldehyde (PFA) for 15 minutes at ambient temperature (and, if necessary, maintained at 4° C.). The cells were permeabilized for 5 minutes with methanol at −20° C., blocked for 1 hour in PBS comprising 2% of BSA (Bovine serum albumin). Immunological markings were done by using the clone 5.8A MyoD1 mouse monoclonal antibody (code DAKO M3512) diluted to 1/100, incubated for one night at 4° C. Next, a goat anti-mouse 488-IgG fluoro Alexa secondary antibody (1/500) was incubated for 1 hour at ambient temperature. The nuclei were marked with DAPI for 5 minutes. The strips were mounted on a Fluoromount G slide and observed under a fluorescence microscope (DM2500 Leica confoncal imaging and ImageJ application).

The efficacy of the myo-conversion was expressed by calculating the percentage of positive nuclei for MyoD1 relative to the positive nuclei with DAPI (100 cells counted per condition).

3. Clinical Product

The vector used for the clinical trials, comprising the sequence JR53 (SEQ ID NO: 3), is the G7U007 bacculoAAV2/8-U7-JR53 vector produced by Gënëthon (lot no. 14P0353: JR53), as described in example 1.

4. Transduction of Human DMD Fibromyoblasts by JR53

Myo-converted fibroblasts (fibromyoblasts) were infected by the vector comprising the JR53 sequence (MOI 300,000 viral genomes per cell) in IMDM medium without serum at 37° C. Five hours later, the fibromyoblasts were differentiated in IMDM medium, doped with 1% of horse serum, 10 µg/mL of gentamycin and 10 µg/mL of doxycyclin for 13 to 14 days. The differentiated cells were scraped in PBS, at ambient temperature, collected in a first tube (intended for a Western-type transfer) and kept on ice. 1/10 of the harvested quantity was transferred for RNA extraction. After 1 minute of centrifugation at 11,000 g, the cell pellets were frozen and stored at −80° C.

5. Exon Skipping Test on the Dystrophin Pre-mRNA in Transduced Human DMD Fibromyoblasts The total RNA was extracted from the cells using the Nucleospin RNAII kit (Macherey Nagel) according to the manufacturer's instructions and eluted in 30 µL of water. Aliquot parts of 500 ng of whole RNA were used for a nested RT-PCR analysis. The reverse transcription reaction was done with a random primer analyzer at 42° C. for 50 min using the Superscript II kit (Life Technologies), then by PCR using the PCR Master mix kit (Promega).

For the evaluation of the exon skipping of the pre-mRNA of DMD, a nested RT-PCR was done (PCR1): 2 µL of cDNA in a total volume of 20 µL with primers surrounding the mutation and exon 53 (see Table 6), for 30 cycles [95° C. (30 sec)-56° C. (1 min)-72° C. (2 min)]. Next, 3 µL of PCR1 in a total volume of 30 µL was amplified for 25 seconds with a 2nd pair of primers (see Table 6).

To evaluate the total mRNA of the dystrophin and the 18S ribosomal mRNA (endogenous control of the addition of cDNA), a single PCR of 34 cycles [95° C. (30 sec)-57° C. (1 min)-72° C. (1 min)] was done with the pair of primers described in Table 6.

The PCR products were analyzed by electrophoresis on 1.8% agarose gel in Tris-acetate-EDTA buffer. The expected sizes for the RT-PCR products are provided in Table 7 below. The number of pixels obtained for each band was treated with the ImageJ software. The bands corresponding to the size of the amplicon having exon skipping (lower band) were cut, purified through a column using the Nucleospin Gel and PCR Clean-up Kit (Macherey Nagel), and sequenced (by GATC).

TABLE 6

List of primers used in the PCR experiments

| Exon skipping | PCR1 | PCR2 |
|---|---|---|
| | GAGAACCTCTTCAGTGACCTAC Dys9-R (SEQ ID NO: 38): GAGGTGGTGACATAAGCAGC | |

TABLE 6-continued

List of primers used in the PCR experiments

| Exon skipping | PCR1 | PCR2 |
|---|---|---|
| 18s ribosomal mRNA | PCR 18S-F/18S-R 18S-F (SEQ ID NO: 35): TCAAGAACGAAAGTCGGAGGTTCG 18S-R (SEQ ID NO: 36): TTATGCTCAATCTCGGGTGGCTG | |

TABLE 7

Anticipated size of the RT-PCR products

Skipping of the exon 53

| Cells | Primers | Parental Amplicon size (bp) | del53 Amplicon size (bp) | Dystrophin Total Size (bp) | 18S Size (bp) |
|---|---|---|---|---|---|
| Healthy and control | F49-R57 | | | 818 | 459 |
| | F50-R56 | 1183 | 971 | | |
| del 52 | F49-R57 | | | 818 | 459 |
| | F50-R56 | 1065 | 853 | | |
| del 50-52 | F49-R57 | | | 818 | 459 |
| | F49-R56 | 796 | 584 | | |
| del 48-52 | F43-F57 | | | 818 | 459 |
| | F44-R56 | 1352 | 1140 | | |
| del 45-52 | F43-F57 | | | 818 | 459 |
| | F44-R56 | 870 | 658 | | |

6. Test of the Expression of the Dystrophin Protein by Western Blot in Transduced DMD Human Fibromyoblasts The cellular proteins were extracted from the lysis buffer (saccharose 125 mM, Tris-HCl 5 mm pH 6.4, XT-tricine migration buffer at 6% (Bio-Rad), SDS at 10%, glycerol at 10%, β-mercaptoethanol at 5%, protease inhibitors). The samples were denatured for 5 minutes at 95° C.

The protein concentration was determined using the BCA Protein Assay Kit (Thermo Scientific Pierce) on 2 μL of protein sample pretreated with the protein assay reagent of the Compat-Able™ kit (Thermo Scientific Pierce). 75 to 100 μg of proteins were loaded on a pre-poured gel with 3-8% of polyacrylamide (Criterion XT Tris-acetate kit by Bio-Rad). The dystrophin was detected by hybridization of the membrane with the NCL-DYS1 primary monoclonal antibody (Novocastra) diluted to 1:50, then incubated with the sheep IgG secondary antibody (HRP) diluted to 1:15,000. The proteins are revealed by the SuperSignal West Pico or Femto Maximum Sensitivity Substrate kit (Thermo Scientific Pierce). The total muscle proteins were revealed by performing a hybridization of the membrane with a rabbit calnexin antibody diluted to 1:2000, for one night at 4° C., then incubation with the goat anti-rabbit IgG secondary antibody (HRP) diluted to 1:50,000.

7. Information on the Cells
7.1. Table of Patients (Table 8):

| GNT Bank Code | Patient Number | Type of Deletion | Number of cells per well |
|---|---|---|---|
| 5-13889 | 01-001 | 48-52 | $1.8 \cdot 10^6$ |
| 5-14211 | 01-009 | 52 | $1.8 \cdot 10^6$ |
| 5-14476 | 01-011 | 45-52 | $1.8 \cdot 10^6$ |
| 5-14496 | 01-014 | 45-52 | $1.6 \cdot 10^6$ |
| 5-14878 | 01-015 | 50-52 | $1.7 \cdot 10^6$ |
| 5-14498 | 01-016 | 48-52 | $1.9 \cdot 10^6$ |
| 5-14499 | 01-017 | 50-52 | $1.6 \cdot 10^6$ |
| 5-14589 | 01-018 | 50-52 | $1.8 \cdot 10^6$ |
| 5-14683 | 01-021 | 48-52 | $1.8 \cdot 10^6$ |
| 5-16283 | 02-002 | 45-52 | $1.83 \cdot 10^6$ |

7.2. Control Cells

The cell lines were provided by the cell immortalization platform of the Centre de Recherche en Myologie [Myology Research Center], at the Université de la Sorbonne UPMC-INSERM-UMRS 974-CNRS FRE 3617—Institut de Myologie [Myology Institute].

Fibromyoblasts

Control of the expression of dystrophin: J5C healthy human fibroblasts, myo-conversion done in the UMRS974 research unit.

Negative control of the restoration of dystrophin: immortalized fibroblasts no. F033 ineligible (stop codon in exon 16) for exon skipping by JR53, myo-conversion done in the UMRS974 research unit.

Immortalized Myoblasts

Healthy myoblasts for the positive control of the expression of dystrophin no. 8220: hM Positive control of the efficacy of the clinical product: DMD myoblasts with a deletion in exon 52 eligible for skipping exon 53, called KM571DMD10FL.

B. Results

1. Conversion of Human DMD Fibroblasts into Fibromyoblasts:

All of the lots of DMD fibroblasts (10/10) were shown to be positive for the nuclear expression of MyoD, showing a percentage of positive nuclei for myoD1 relative to the total number of marked nuclei greater than 70% (Table 9), therefore able to be considered myo-converted.

TABLE 9

Conversion of human DMD fibroblasts into fibromyoblasts (average of the percentages of the myo-conversion for two independent experiments)

| GNT Bank Code | Patient Number | Patient Code | Type of Deletion | Myo-conversion rate | Myo-conversion average |
|---|---|---|---|---|---|
| 5-13889 | 01-001 | BAS SA | 48-52 | 95%-100% | 98 +/- 2.5% |
| 5-14211 | 01-009 | RYF NI | 52 | 93%-99% | 96 +/- 3% |
| 5-14476 | 01-011 | GRA IO | 45-52 | 100%-100% | 100 +/- 0% |
| 5-14496 | 01-014 | DOR AL | 45-52 | 100%-100% | 100 +/- 0% |
| 5-14878 | 01-015 | TUD PE | 50-52 | 100%-100% | 100 +/- 0% |
| 5-14498 | 01-016 | BEC MA | 48-52 | 68%-90% | 79 +/- 11% |
| 5-14499 | 01-017 | MAR DR | 50-52 | 89%-86% | 88 +/- 1.5% |
| 5-14589 | 01-018 | DHO RO | 50-52 | 92%-92% | 92 +/- 0% |

TABLE 9-continued

Conversion of human DMD fibroblasts into fibromyoblasts (average of the percentages of the myo-conversion for two independent experiments)

| GNT Bank Code | Patient Number | Patient Code | Type of Deletion | Myo-conversion rate | Myo-conversion average |
|---|---|---|---|---|---|
| 5-14683 | 01-021 | RIC JU | 48-52 | 64%-90% | 77 +/− 13% |
| 5-16283 | 02-002 | GRA EY | 45-52 | 79%-86% | 83 +/− 3.5% |
| F033 DMD 16 control | | | stop in exon 16 | 79%-90% | 85 +/− 5.5% |

2. Efficacy of JR53 for Skipping Exon 53 in Transduced DMD Human Fibromyoblasts

Figure 6:
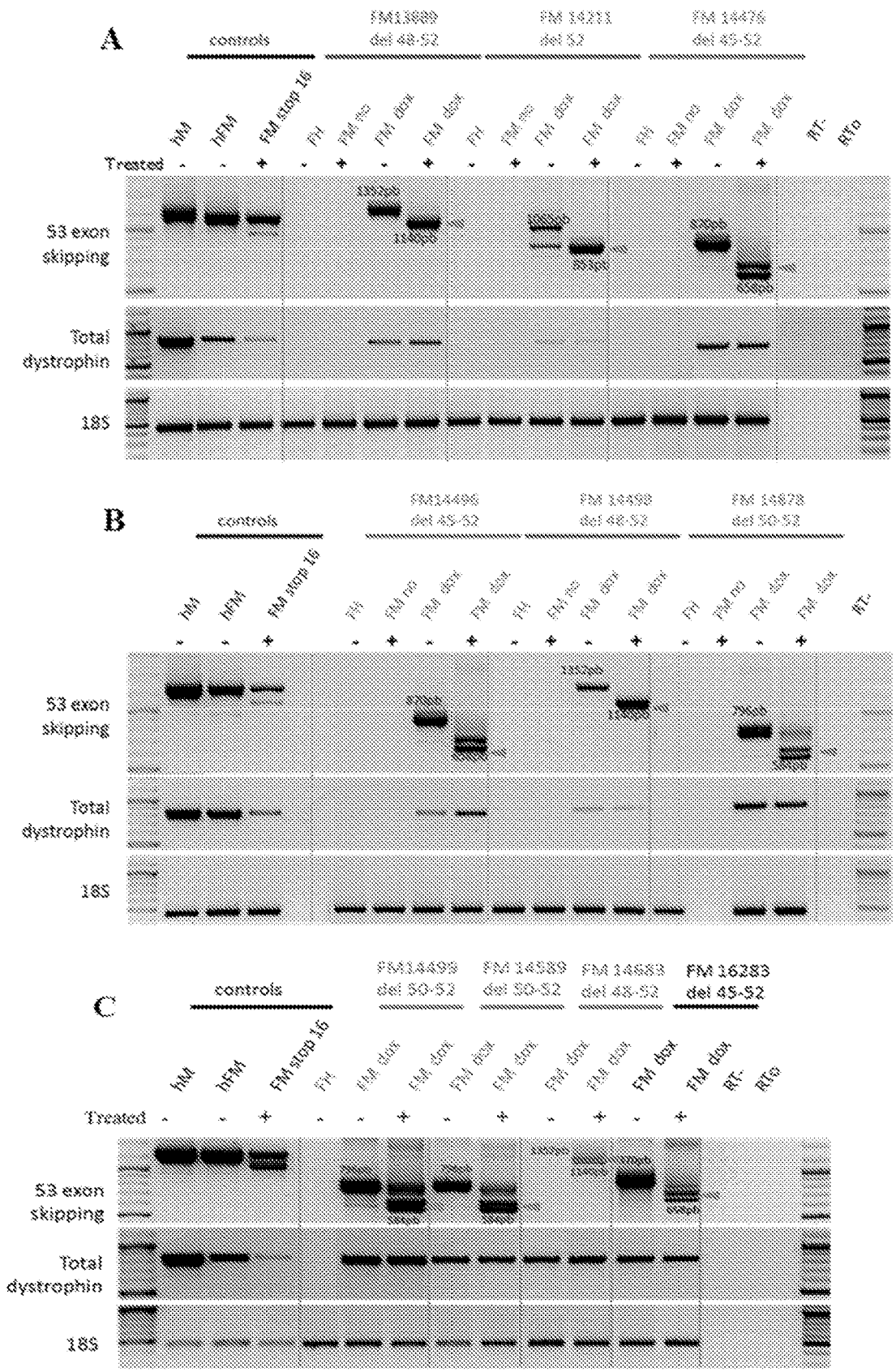
FIGS. 6A-6B: Efficacy of JR53 for skipping exon 53 of dystrophin in transduced DMD human fibromyoblasts.
FIG. 6C: from left to right: molecular weight marker; healthy control myoblasts (hM); fibromyoblasts (hFM); non-eligible DMD fibromyoblasts (FMstop16); control DMD fibroblasts (FH), fibromyoblasts induced by doxycyclin of 4 DMD patients 5-14499 (FM14499 del50-52), 5-14589 (FM14589 del50-52), 5-14683 (FM14683 del48-52), 5-16283 (FM16283 del45-52), with 2 conditions for each: not treated with JR53 (FM dox−), treated with JR53 (FM dox+); negative control of the reverse transcription without superscript enzyme (RT−) or without RNA (RTo); molecular weight marker.

The efficacy of JR53 for exon skipping was tested in two or three experiments for each lot of DMD fibromyoblasts. RT-PCR products corresponding to the expected size without exon 53 were detected in each of the 10 DMD patients (FIG. 6).

The efficacy percentage of JR53 was calculated using the ratio between the number of pixels obtained for the skipped band and the sum of the pixels calculated for all of the skipped and non-skipped bands (Table 10).

For 8 of the lots of DMD fibromyoblasts, the efficacy of JR53 was detected as being greater than 70%, while for patients 5-14878 DMD and 5-14499 DMD, the efficacy was lower with an efficacy of 64 and 50%, respectively. The bands corresponding to the size of the amplicon having exon skipping (lower band) were sequenced and were all given the expected sequence corresponding to the skipping of exon 53.

TABLE 10

Efficacy of JR53 for skipping exon 53 in human DMD fibromyoblasts

| GNT Bank Code | Patient Number | Patient Code | Type of Deletion | % of skipping of exon 53 | | | Average in % of skipping of exon 53 | Number of experiments (n) |
|---|---|---|---|---|---|---|---|---|
| 5-13889 | 01-001 | BAS SA | 48-52 | 100 | 83 | 100 | 94 | n = 3 |
| 5-14211 | 01-009 | RYF NI | 52 | 100 | 72 | 67 | 80 | n = 3 |
| 5-14476 | 01-011 | GRA IO | 45-52 | 100 | 75 | | 88 | n = 2 |
| 5-14496 | 01-014 | DOR AL | 45-52 | 100 | 82 | | 91 | n = 2 |
| 5-14878 | 01-015 | TUD PE | 50-52 | 60 | 72 | 60 | 64 | n = 3 |
| 5-14498 | 01-016 | BEC MA | 48-52 | 100 | 84 | | 92 | n = 2 |
| 5-14499 | 01-017 | MAR DR | 50-52 | 52 | 48 | | 50 | n = 2 |
| 5-14589 | 01-018 | DHO RO | 50-52 | 61 | 77 | 82 | 73 | n = 3 |
| 5-14683 | 01-021 | RIC JU | 48-52 | 73 | 72 | | 73 | n = 2 |
| 5-16283 | 02-002 | GRA EY | 45-52 | 76 | 100 | | 88 | n = 2 |

3. Restoration of the Expression of the Dystrophin Protein in DMD Human Fibromyoblasts The results of the Western blots done appear in FIG. 7.

The restoration level of the expression of the dystrophin in the human DMD fibromyoblasts was evaluated by the quantification of the number of pixels corresponding to the signal of each band using the ImageJ software. The dystrophin level was normalized owing to the expression of the calnexin (contribution of total proteins). The percentage of restored dystrophin was calculated using the ratio between the normalized dystrophin level in the treated fibromyoblasts and the expression rate of the dystrophin observed in the healthy fibromyoblasts (hFM), considered to represent 100%. The results show that the restoration of the dystrophin protein could be observed in all of the lots of DMD fibromyoblasts treated with JR53. It must be noted that for subject DMD 5-14889, the evaluation of the restored dystrophin level was only measured once.

The quantification of the restoration data for the expression of the dystrophin protein is shown in Table 11:

TABLE 11

Quantification of the restoration of the dystrophin protein in transduced DMD human fibromyoblasts

| GNT Bank Code | Patient Number | Patient Code | Type of Deletion | Restoration of the dystrophin protein (%) | | | Average (%) | Number of experiments (n) |
|---|---|---|---|---|---|---|---|---|
| 5-13889 | 01-001 | BAS SA | 48-52 | 96 | 13 | 9 | 39 | n = 3 |
| 5-14211 | 01-009 | RYF NI | 52 | 18 | 28 | | 23 | n = 2 |
| 5-14476 | 01-011 | GRA IO | 45-52 | 100 | 35 | | 68 | n = 2 |
| 5-14496 | 01-014 | DOR AL | 45-52 | 24 | 23 | | 23.5 | n = 2 |
| 5-14878 | 01-015 | TUD PE | 50-52 | 57 | 31 | 41 | 43 | n = 3 |

TABLE 11-continued

Quantification of the restoration of the dystrophin protein in transduced DMD human fibromyoblasts

| GNT Bank Code | Patient Number | Patient Code | Type of Deletion | Restoration of the dystrophin protein (%) | | Average (%) | Number of experiments (n) |
|---|---|---|---|---|---|---|---|
| 5-14498 | 01-016 | BEC MA | 48-52 | 93 | 49 | 71 | n = 2 |
| 5-14499 | 01-017 | MAR DR | 50-52 | 42 | 0 | 17 29.5 | n = 2 |
| 5-14589 | 01-018 | DHO RO | 50-52 | 6 | 0 weak signal | 6 | n = 2 |
| 5-14683 | 01-021 | RIC JU | 48-52 | 47 | 39 | 43 | n = 2 |
| 5-16283 | 02-002 | GRA EY | 45-52 | 38 | 20 | 29 | n = 2 |

CONCLUSIONS

All of the results obtained in the context of this study done on human fibromyoblasts taken from patients with different forms of DMD are summarized in Table 12 below:

TABLE 12

Summary of the JR53 efficacy data on human DMD fibromyoblasts.

| GNT Bank Code | Patient Number | Patient Code | Type of Deletion | Myo-conversion in % | Skipping of exon 53 in % | Restoration of the dystrophin in % |
|---|---|---|---|---|---|---|
| 5-13889 | 01-001 | BAS SA | 48-52 | 98 | 94 | 39 |
| 5-14211 | 01-009 | RYF NI | 52 | 96 | 80 | 23 |
| 5-14476 | 01-011 | GRA IO | 45-52 | 100 | 88 | 68 |
| 5-14496 | 01-014 | DOR AL | 45-52 | 100 | 91 | 23 |
| 5-14878 | 01-015 | TUD PDE | 50-52 | 100 | 64 | 43 |
| 5-14498 | 01-016 | BEC MA | 48-52 | 79 | 50 | 71 |
| 5-14499 | 01-017 | MAR DR | 50-52 | 88 | 50 | 29 |
| 5-14589 | 01-018 | DHO RO | 50-52 | 92 | 73 | 6 |
| 5-14683 | 01-021 | RIC JU | 48-52 | 77 | 73 | 43 |
| 5-16283 | 02-002 | GRA EY | 45-52 | 83 | 88 | 29 |

In conclusion, the preclinical results obtained for different forms of DMD (Δ52, Δ45-52, Δ48-52 and Δ50-52) presented above validate the therapeutic potential of the JR53 antisense carried by the tested construction.

What is claimed is:

1. A recombinant adeno-associated viral vector (AAVr) comprising a sequence coding an antisense oligonucleotide (AON) complementary to a +30 to +69 region of exon 53 of a pre-messenger RNA (pre-mRNA) of dystrophin, wherein the sequence coding the AON comprises a nucleic acid sequence as set forth in SEQ ID NO: 3.

2. The AAVr vector according to claim 1, wherein the AON allows skipping of exon 53 on the pre-mRNA of the dystrophin.

3. The AAVr vector according to claim 1, wherein the sequence coding the AON has less than 70 bases.

4. The AAVr vector according to claim 1, wherein the sequence coding the AON is inserted in a sequence coding a modified small nucleotide RNA (snRNA).

5. The AAVr vector according to claim 4, wherein the modified snRNA is of type U7 (U7snRNA).

6. The AAVr vector according to claim 5, wherein the modified snRNA comprises a nucleic acid sequence set forth in SEQ ID NO: 2.

7. The AAVr vector according to claim 1, wherein the vector is selected from the group consisting of AAV2/1, AAV2, AAV2/6, AAV2/8, AAV2/9, AAV2/10, AAV8 and AAV9.

8. A pharmaceutical composition comprising an AAVr vector according to claim 1 and a pharmaceutically acceptable carrier.

9. The AAVr vector according to claim 1 formulated for administration as a medicinal drug.

10. A method of treating Duchenne muscular dystrophy (DMD), comprising administering the AAVr vector according to claim 1 to a subject in need thereof.

11. The method according to claim 10, wherein the DMD is of form that has a deletion of exon 52 (Δ52), exons 45-52 (Δ45-52), exons 48-52 (Δ48-52), or exons 50-52(Δ50-52).

12. The AAVr vector according to claim 3, wherein the sequence coding the AON has less than or equal to 50 bases.

13. The AAVr vector according to claim 5, wherein the modified snRNA is of murine origin.

14. The AAVr vector according to claim 1, wherein the vector is AAV2/8.

15. The AAVr vector according to claim 1, wherein the pre-mRNA of dystrophin is of human origin.

* * * * *